United States Patent [19]
Kuzma et al.

[11] Patent Number: 5,266,325
[45] Date of Patent: Nov. 30, 1993

[54] PREPARATION OF HOMOGENEOUS HYDROGEL COPOLYMERS

[75] Inventors: Petr Kuzma, Monmouth Junction; Daniel G. Moro, Randolph; Harry Quandt, North Middletown, all of N.J.

[73] Assignee: Hydro Med Science Division of National Patent Development Corp., New York, N.Y.

[21] Appl. No.: 621,346

[22] Filed: Dec. 3, 1990

Related U.S. Application Data

[63] Continuation-in-part of Ser. No. 589,957, Sep. 28, 1990, abandoned.

[51] Int. Cl.$^5$ .............................. A61M 5/178
[52] U.S. Cl. .................................. 424/422; 424/423; 264/310; 264/311; 264/255; 264/267; 523/526; 604/59
[58] Field of Search .................. 604/57, 59, 60, 64, 604/59; 424/473, 78, 464, 422, 423; 523/526; 264/310, 311, 255, 267

[56] References Cited

U.S. PATENT DOCUMENTS

| | | | |
|---|---|---|---|
| 2,513,014 | 6/1950 | Fields | 604/60 |
| 3,921,632 | 11/1975 | Bardani | 604/60 |
| 4,846,793 | 7/1989 | Leonard | 604/60 |
| 4,871,094 | 4/1988 | Gall | 604/59 |
| 4,959,217 | 9/1990 | Sanders | 424/473 |
| 4,994,028 | 2/1991 | Leonard | 604/59 |
| 5,004,614 | 4/1991 | Staniforth | 424/78 |
| 5,035,891 | 7/1991 | Runk et al. | 424/473 |

FOREIGN PATENT DOCUMENTS

| | | |
|---|---|---|
| 0246653 | 11/1987 | European Pat. Off. |
| 0384646 | 8/1990 | European Pat. Off. |
| 1306541 | 2/1973 | United Kingdom |

*Primary Examiner*—Thurman K. Page
*Assistant Examiner*—Raj Bawa
*Attorney, Agent, or Firm*—Howson and Howson

[57] ABSTRACT

A method is provided for the preparation of homogeneous copolymers having a predetermined equilibrium water content (EWC) value formed by the addition polymerization of a mixture of ethylenically unsaturated monomer A and ethylenically unsaturated monomer B, for example, 2-hydroxyethyl methacrylate and hydroxypropyl methacrylate. The method requires determining the EWC values of the hydrogel homopolymer of hydrophilic monomer A (homopolymer A) and the hydrogel homopolymer of hydrophilic monomer B (homopolymer B); determining the relationship of the EWC values of the homogeneous copolymers AB versus the chemical composition of said copolymers AB; selecting the targeted EWC value and determining the chemical composition of copolymer AB having the targeted EWC value; forming a polymerizable mixture of monomer A and monomer B in amounts sufficient to yield copolymer AB having the targeted EWC value; and effect the polymerization reaction to yield copolymer AB characterized by the targeted EWC value. A method is also provided for the preparation of a delivery device including a drug contained in the reservoir of the hydrogel of copolymer AB, said device being characterized by its capability of eluting or releasing the drug through the hydrogel membrane to a delivery environment at a predetermined rate. There is also disclosed a sterilized kit containing a trocar or hypodermic needle/syringe and the aforesaid drug delivery device having a cylindrical shape with a rounded or bullet-like extremity.

40 Claims, 12 Drawing Sheets

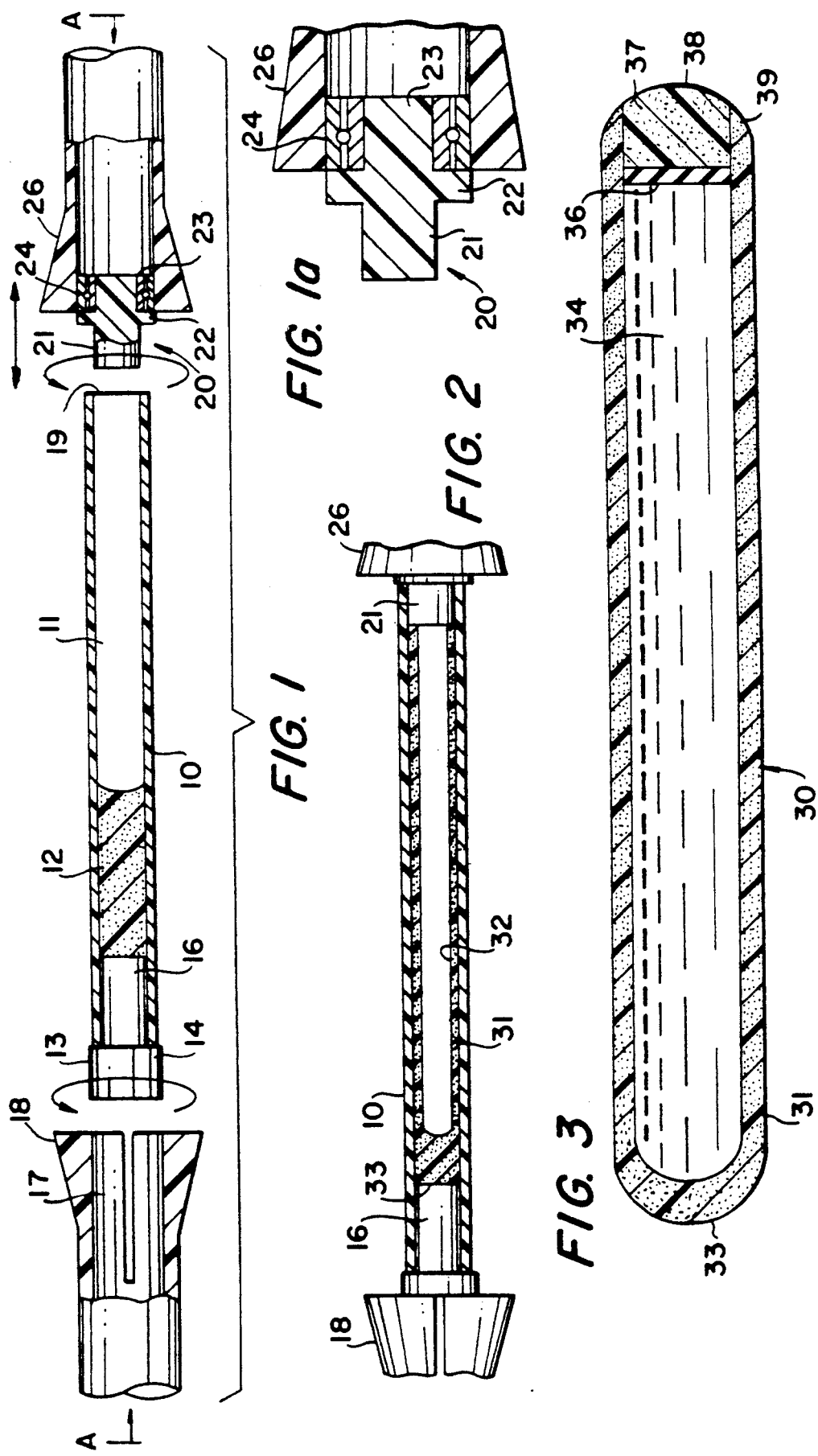

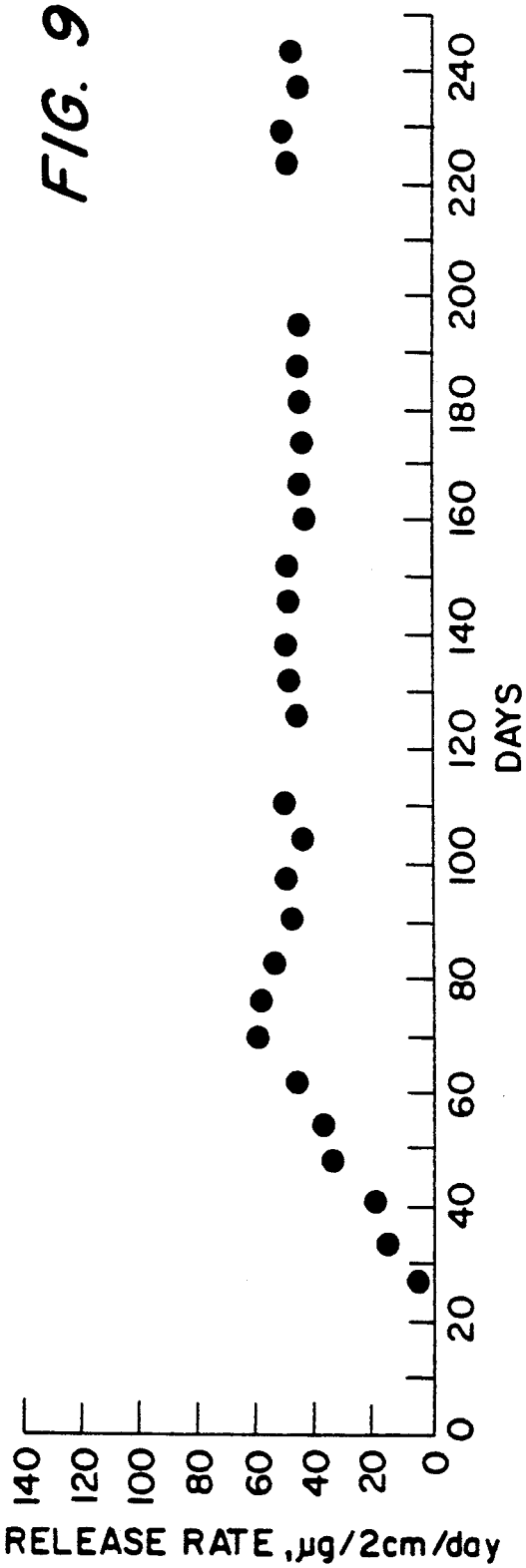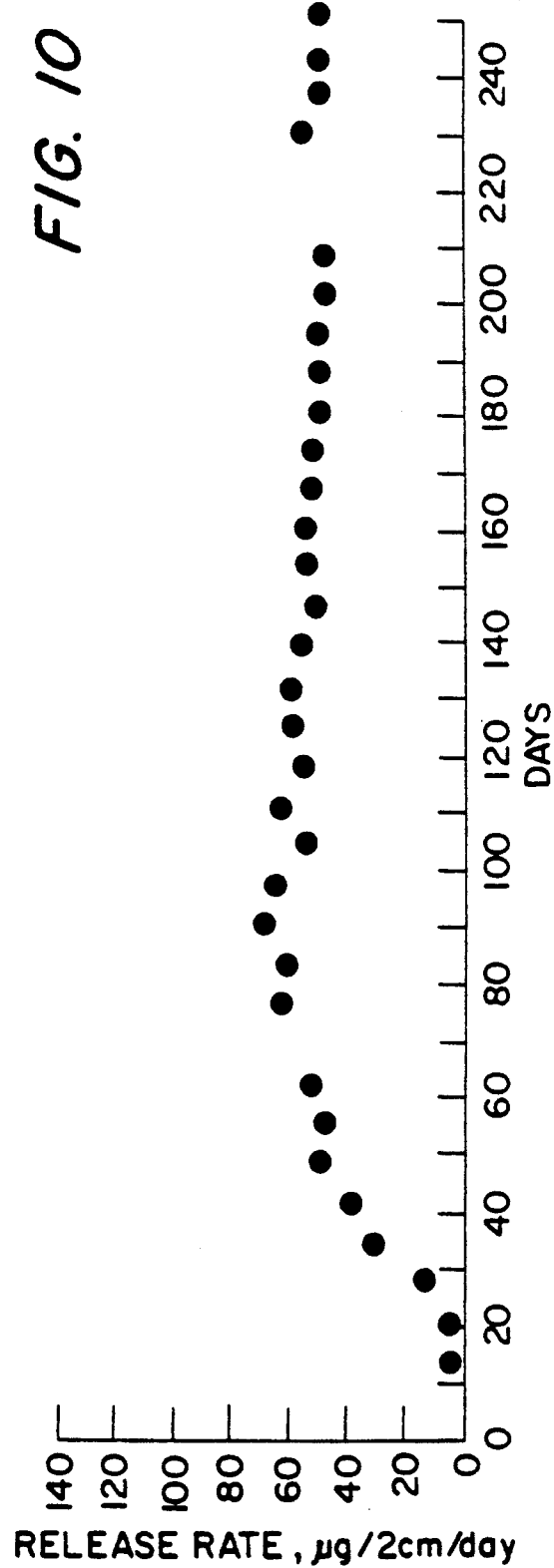

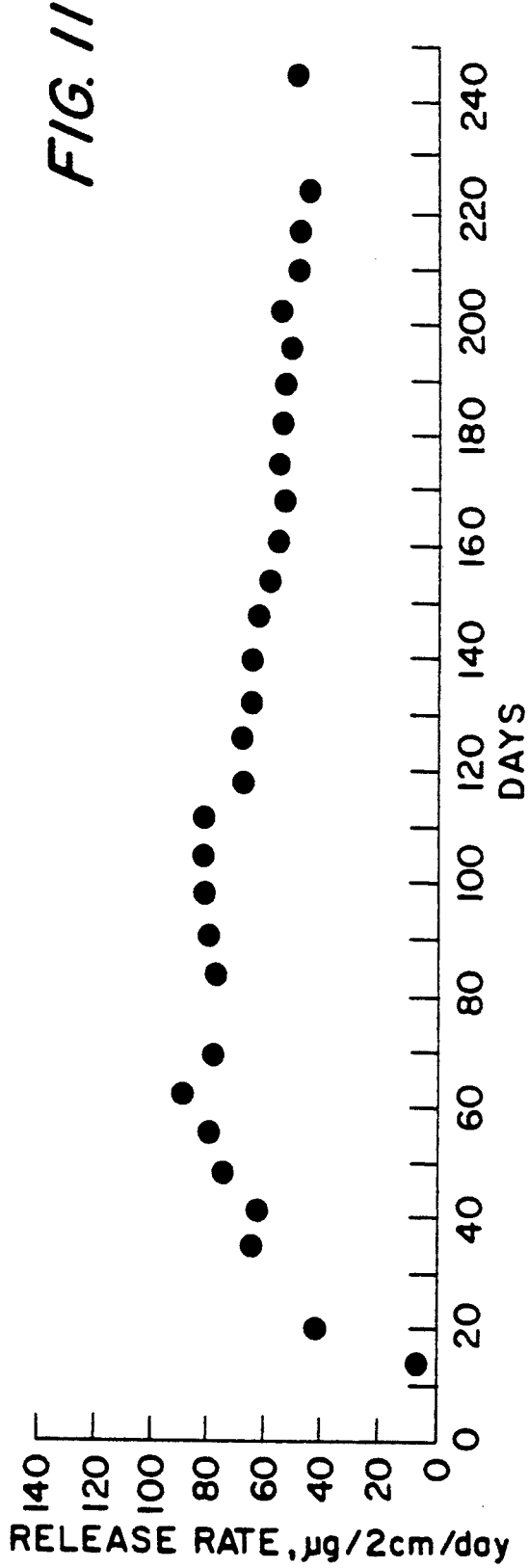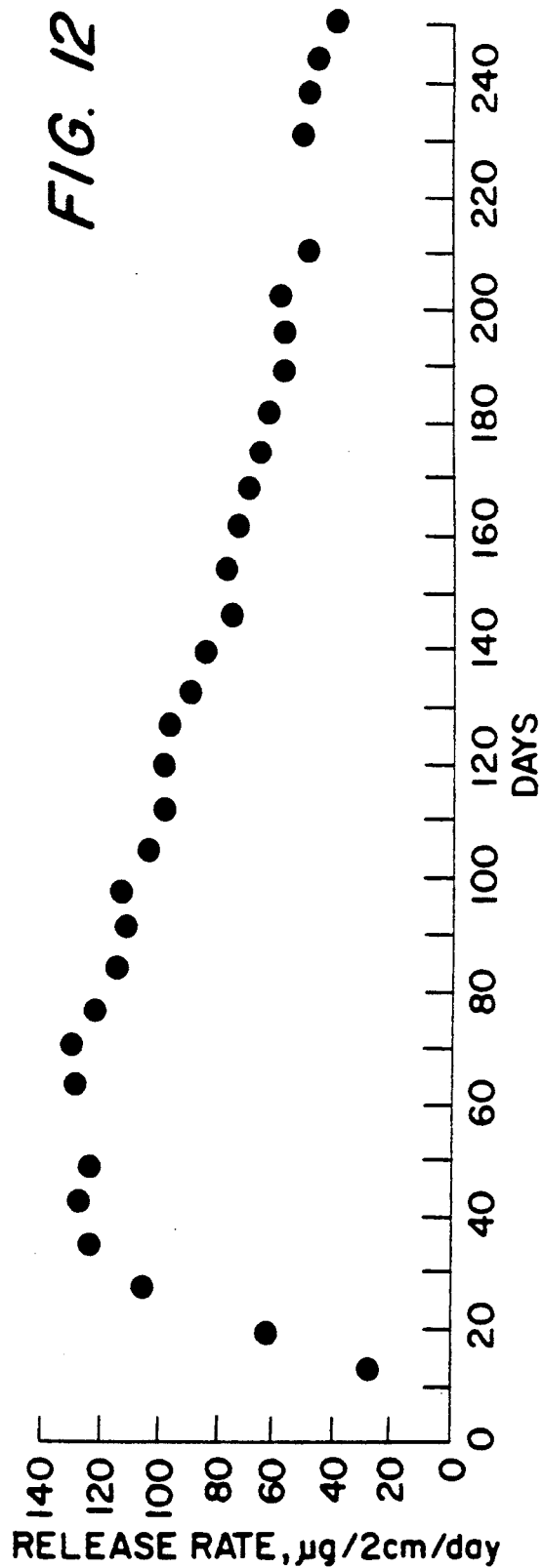

PREPARATION OF HOMOGENEOUS HYDROGEL COPOLYMERS

CROSS-REFERENCE TO RELATED APPLICATION

This application is a continuation-in-part of U.S. Ser. No. 07-589,957 filed Sep. 28, 1990, entitled "Manufacture of Water-Swellable Hydrophilic Articles and Drug Delivery Devices" in the names of Daniel G. Moro, Petr Kuzma, and Harry Quandt, both of said applications being assigned to the same assignee, and now abandoned.

DESCRIPTION

The present invention relates to a method for the preparation of homogeneous hydrogel copolymers which are useful as a hydrogel membrane in the diffusion therethrough of active compounds in aqueous media. In one aspect, the invention relates to water-insoluble, water-swellable, homogenous hydrogel copolymers of 2-hydroxyethyl methacrylate (HEMA) and at least one ethylenically unsaturated hydrophilic monomer copolymerizable therewith which are especially adaptable for use in drug delivery devices such as body implants whereby the contained drug is diffused through the hydrogel copolymer membrane to the body environment at a predetermined rate.

BACKGROUND OF THE INVENTION

It is well-known in the literature that ethylenically unsaturated hydrophilic monomers with/without additional ethylenically unsaturated hydrophobic monomers can be polymerized to prepare hydrogel polymers. The literature is also replete with studies demonstrating the diffusion of active compounds, e.g., drugs, across a hydrogel membrane to the delivery environment.

U.S. Pat. No. 3,767,790 discloses the preparation of products whereby microorganism(s), e.g., bacteria or yeast, can be entrapped in a hydrophilic polymer, in the form of a powder, tablet, pill or capsule, for release into an environment on which the microorganism(s) can act. Water-swellable polymers of 2-hydroxyethyl methacrylate alone or in combination with acrylamide or vinylpyrrolidone are illustrative of the many polymer matrices disclosed by the patentee.

U.S. Pat. No. 3,808,686 discloses the preparation of an organic solution of a water-insoluble, organic solvent soluble hydrophilic polymer for application to denture prostheses to eliminate denture breath. Among the numerous polymers disclosed are homopolymers of 2-hydroxyethyl methacrylate and of 2-hydroxyethyl acrylate; copolymers of 2-hydroxyethyl acrylate and methyl methacrylate; copolymers of 2-hydroxyethyl methacrylate and vinylpyrrolidone; and others. The patentee discloses the dissolution of the polymer in a suitable non-toxic volatile solvent such as ethyl alcohol to which a water-soluble flavoring agent or fragrance is added.

U.S. Pat. No. 3,780,003 discloses moisture vapor permeable films and coatings of copolymers of hydroxyalkyl methacrylate or of hydroxyalkyl acrylate with alkoxyalkyl methacrylate or of alkoxyalkyl acrylate. Examples include copolymers of 2-hydroxyethyl methacrylate and methoxyethyl acrylate, of 2-hydroxyethyl methacrylate and ethoxyethyl acrylate, and of hydroxyethyl acrylate and ethoxyethyl methacrylate. The polymers, as films and coatings, have utility in adhesive, medical and surgical areas.

U.S. Pat. No. 4,298,002 discloses hydrophilic materials useful in the preparation of chambers and devices for the release of biologically active tissue contained therein. Illustrative polymers include those made from mixtures of 2-hydroxyethyl methacrylate and monomers such as N-vinylpyrrolidone, acrylamide, and others, plus ethylene glycol dimethacrylate as a crosslinking agent.

U.S. Pat. No. 3,660,563 discloses water-soluble polymers containing fragrances, drugs, soaps, etc. entrapped therein. Polymers of hydroxy($C_2$–$C_3$)alkyl acrylate or of hydroxy($C_2$–$C_3$)alkyl methacrylate and an ethylenically unsaturated copolymerizable monomer are disclosed. The copolymerizable monomer is employed in an amount sufficient to produce a water-soluble copolymer.

U.S. Pat. No. 4,303,066 discloses particulate water-swellable, water-insoluble, alcohol swellable particulate polymers of hydroxyalkyl acrylate, of hydroxyalkyl methacrylate, of vinylpyrrolidone, and/or of alkoxyalkyl methacrylate. The particulate homopolymer or copolymer is employed in a two package system useful in the formation of a burn dressing.

U.S. Pat. No. 3,641,237 discloses the preparation of hydrophilic polymeric films having good diffusion barriers for water-soluble or water-leachable drugs. The films are prepared by polymerizing at least one alkoxyalkyl methacrylate or alkoxyalkyl acrylate with/without a minor amount of 2-hydroxyethyl methacrylate or hydroxypropyl acrylate.

U.S. Pat. No. 4,517,138 discloses the preparation of hydrogel contact lenses prepared by spincasting a mixture containing 2-hydroxyethyl methacrylate with/without acrylamide.

In the administration of certain pharmaceuticals, long-term drug delivery has been shown to be effective in that constant serum levels are obtained and patient compliance is improved. Delaying the release of the active agent from a drug delivery device is also desirable in that an immediate release upon placement in the delivery environment can result in unacceptably high initial concentrations of a drug at the sites of implantation.

The examination of synthetic hydrogels for potential biomedical applications (including potential use in certain drug delivery devices) has given rise to various theories regarding mechanisms of diffusion. Lee, Jhon and Andrade have proposed that there are three classes of water in hydrogels, using poly(2-hydroxyethyl methacrylate), oftentimes abbreviated as polyHEMA, as their model [*Nature of Water in Synthetic Hydrogels, J. Colloid & Interface Sci.*, 51 (2): 225–231 (1975)]. The first 20% of hydrogel water content, called "Z water", was said to be bound to the polymer matrix. The next 10–12% of water content, called interfacial or "Y water", is partially affected by the polymer matrix. Any additional water imbibed by the gel is relatively unaffected by the polymer matrix; it is called bulk or "X water".

The Lee, et al. model was expanded upon by Kim, Cardinal, Wisniewski and Zentner [*Solute Permeation Through Hydrogel Membranes: Hydrophilic vs. Hydrophobic Solutes, ACS Symposium Series (Water in Polymers)*, 127 (20): 347–359 (1980)]. They concluded that the diffusion coefficients for hydrophilic solutes through hydrogel membranes depends on molecular size and water content; permeation in pure polyHEMA and in polyHEMA crosslinked with a low mole percent of ethylene glycol dimethacrylate was via the pore mechanism, i.e., through the bulk-type water. Hydrophobic solutes were said to diffuse via both pore and partition mechanisms, i.e., respectively through the bulk-type water, and through the interfacial-type and bound-type water.

Wood, Attwood and Collett have described a model for diffusion of the small hydrophobic molecule salicylic acid (the solute) in hydrogels [*The Influence of Gel Formulation on the Diffusion of Salicylic Acid in PolyHEMA Hydrogels, J. Pharm. Pharmacol.*, 34: 1–4 (1982)]. Radioactively labeled salicylic acid was added to a HEMA monomer solution and polymerized in situ. The water contents of the resulting gels were measured. Diffusion was measured by quantifying migration of the solute to a gel placed in contact with the sample gels. It was concluded that diffusion occur ed primarily through the polymer's pores via the hydrating liquid at higher levels of hydration (more than 31%). At hydration levels below 31%, diffusion was said to occur by dissolution of the solute within the polymer segments; crosslinker concentration did not have any significant effect on diffusion. This was correlated to a change in pore size proportional with percent hydration. For another treatment of the interaction of pore size and diffusion, see Wisniewski and Kim [*J. Membrane Sci.*, 6: 299–308 (1980)].

Microporous membranes (some including hydrogels) have been used as rate-limiting barriers for such devices, including implants, ocular inserts, coated intrauterine devices and the like, for example, as described in U.S. Pat. Nos. 3,416,530, 3,618,604, and 3,828,777 to Ness; U.S. Pat. No. 3,551,556 to Kliment, et al; U.S. Pat. No. 4,548,990 to Mueller, et al.

In U.S. Pat. Nos. 3,993,072, 3,948,254, and 3,854,380 to Zaffaroni, drug delivery systems are disclosed including a solid inner matrix containing a drug and surrounded by a wall formed of a polymeric membrane (the '072 and '254 patents call for a microporous membrane, the pores of which contain a drug-release-rate-controlling medium).

Some sustained release devices have been described for the delivery of hydrophilic macromolecules, such as polypeptides. For example, European Patent Application Publication No. 0,092,918 to Churchill, et al. entitled "Continuous Release Formulations" describes the continuous release of, e.g., luteinizing hormone-releasing hormone, growth hormones and growth hormone releasing factor, from a hydrophobic/hydrophilic non-crosslinked copolymer in which the hydrophobic component is biodegradable and the hydrophilic component may or may not be biodegradable. The composition is described as being capable of absorbing water to form a hydrogel when placed in an aqueous, physiological-type environment.

In European Patent Application Publication No. 0246653, publication date Nov. 25, 1987, in the names of Sanders and Domb, there is disclosed a drug delivery device comprising a pharmaceutically acceptable carrier, macromolecules of at least 1000 molecular weight, e.g., luteinizing hormone-releasing hormone polypeptide and analogs thereof, mixed with said carrier, and a non-biodegradable, hydrogel rate-limiting membrane which surrounds or envelopes the drug and carrier. The patent applicants disclose that a ratio of crosslinked and uncrosslinked polymers made from 50–100 mole percent hydrophilic monomers, 0–50 mole percent hydrophobic monomers, and 0–10 mole % crosslinker can be varied to prepare the membrane to the macromolecular composition to be dispensed. The patent applicants state:

"For example, a non-crosslinked hydrophilic homopolymer would be expected to have the largest pore sizes and greatest ability to swell, but ultimately, may tend to dissolve. The addition of crosslinking agent would render the hydrogel somewhat more rigid and limit the swellability of the hydrogel, thereby limiting the expansion of the interstitial spaces. The addition of the hydrophobic comonomer would enhance the restriction even further."

The patent applicant's working examples disclose the preparation of crosslinked and non-crosslinked homopolymers of 2-hydroxyethyl methacrylate and copolymers of 2-hydroxyethyl methacrylate and methyl methacrylate.

Davidson, Domb, Sanders, and McRae disclose that hydrogel membranes of polyHEMA and HEMA/methyl methacrylate copolymer can be used for controlled delivery of analogs of LHRH. Cylindrical implant devices of crosslinked poly(2-hydroxyethyl methacrylate) containing excess LHRH analog (RS-49947) dispersed in silicone oil were implanted in several beagles for one year. Several of the devices, because of the low mechanical strength of the hydrogel polymer, did not remain intact for the whole year; however, of those devices remaining intact estrus was suppressed in the female beagles [Hydrogels for Controlled Release of Peptides, Proceed. Intern. Symp. Cont. Rel. Bioact. Mater., 15, (1988), Controlled Release Society, Inc.].

DESCRIPTION OF THE INVENTION

The invention relates to a method of preparing a homogeneous hydrophilic copolymer having a predetermined equilibrium water content (hereinafter oftentimes referred to as "EWC") value formed by the addition polymerization of a mixture containing ethylenically unsaturated hydrophilic monomer A and an ethylenically unsaturated hydrophilic monomer B copolymerizable therewith, said copolymer being useful as a hydrogel membrane in the diffusion therethrough of a selected active compound in an aqueous medium at a predetermined rate which comprises:

a. determining the EWC values of hydrogel homopolymer of monomer A ("homopolymer A") and hydrogel homopolymer of monomer B ("homopolymer B");

b. determining the relationship of the EWC values of the homogeneous hydrogel copolymers of mixtures of monomer A and monomer B ("copolymers AB") versus the chemical composition of said copolymers AB;

c. selecting the targeted EWC value and determining the chemical composition of homogeneous copolymer AB having this targeted EWC value;

d. forming a polymerizable mixture containing said monomer A and said monomer B in amounts sufficient to yield said homogeneous copolymer AB having the targeted EWC value;

e. subjecting said polymerizable mixture to polymerization conditions for a period of time sufficient to form said homogeneous copolymer AB having the targeted EWC value for use as a hydrogel membrane in the diffusion therethrough of a selected active compound in an aqueous medium at a predetermined rate.

In a most preferred aspect, the invention relates to a method of preparing homogenous hydrophilic copolymers of 2-hydroxyethyl methacrylate ("HEMA") and hydroxypropyl methacrylate ("HPMA") for applications described herein.

In an objective, therefore, to tailor-make homogenous hydrophilic copolymers AB with predetermined EWC values to allow a selected active compound, e.g., a drug, to diffuse through hydrogel membranes fabricated of such copolymers AB at sustained, predetermined rates. The hydrogel copolymer matrix consists essentially of recurring hydrophilic units and, at EWC values in the range of from about 20-25 to about 70-75 weight percent, have a low copolymer-water interfacial free energy. Such copolymers in the form of hydrogel implants exhibit excellent biocompatibility and good resistance to calcification and thus are preferred.

It is known to prepare crosslinked hydrogel polyHEMA using varying concentrations of crosslinking agent, e.g., ethylene glycol dimethacrylate ("EGDMA"). EPO Publication No. 0246653 discussed previously discloses a series of non-crosslinked and crosslinked homopolymers of HEMA having EWC values ranging from 39.1 weight % for non-crosslinked polyHEMA to 22.8 weight % for polyHEMA crosslinked with 5 mole % EGDMA. Lowering the EWC value of hydrogel polymers of HEMA by methods which involve increasing the concentration of a crosslinking agent such as EGDMA and/or by adding an ethylenically unsaturated hydrophobic comonomer, e.g., methyl methacrylate, to the polymerization mixture, introduces undesirable hydrophobic segments in the hydrogel polymer of HEMA. Progressively increasing EGDNU crosslinks in the homopolymers of HEMA increases the brittleness and decreases the flexibility characteristics of the homopolymers. These homopolymers of HENU are more properly considered to be heterogeneous copolymers of HEMA and EGDMA.

The polymerization of a mixture of HEMA, a hydrophobic comonomer, and a crosslinking agent yields a non-homogeneous copolymer (in terms of polarity). This characteristic is especially undesirable when utilizing a non-polar crosslinking agent such as EGDMA in the polymerization mixture since it will tend to concentrate during polymer formation in the non-polar hydrophobic regions of the resulting copolymer causing a crosslinking density gradient therein. The copolymer, being heterogeneous in its structure, is characterized by over-crosslinking in the hydrophobic segments and by under-crosslinking in the hydrophilic segments, thereby imparting weak and fragile properties to the polymer. Further, the interfacial free energy values of the heterogeneous crosslinked copolymers are markedly greater than the values assigned to lightly crosslinked polyHEMA.

In one embodiment, the invention relates to a method of preparing a uniform, homogeneous, water-insoluble, water-swellable copolymeric cylindrically-shaped article with a concentric core having a predetermined equilibrium water content value, said article formed by the addition polymerization of a mixture containing ethylenically unsaturated hydrophilic monomer A and ethylenically unsaturated monomer B copolymerizable therewith, said copolymeric article being useful in a delivery device for the sustained release of an active agent therefrom to a delivery environment which comprises:

a. forming a polymerizable liquid mixture containing monomer A and monomer B in amounts sufficient to yield a homogeneous copolymer AB having a predetermined equilibrium water content value;

b. introducing into the open end of a polymerization column a predetermined amount of said polymerizable liquid mixture;

c. rotating said polymerization column about its longitudinal axis maintained substantially parallel to the ground at a speed sufficient to cause radially outward displacement of said polymerizable liquid mixture to assume a predetermined hollow cylindrical liquid configuration within said column;

d. maintaining the polymerization column under polymerization conditions to convert said polymerizable mixture of predetermined liquid configuration into a predetermined solid hollow cylindrical configuration; and e. recovering a copolymeric cylindrically-shaped article having the predetermined equilibrium water content value and further characterized by a cylindrical core or reservoir and smooth internal and external cylindrical surfaces of substantially uniform thickness between said surfaces.

In one aspect, the invention relates to a method of preparing a uniform, cylindrically-shaped copolymeric cartridge characterized by a predetermined EWC value, by substantial uniformity of thickness between its outer and inner cylindrical surfaces (Do minus Di equals a constant value and wherein Do represents the outer diameter of the cartridge and Di represents the inner diameter of the cartridge), and by a pore-forming agent uniformly or homogeneously distributed throughout the cartridge. In this aspect of the invention, a uniform or homogeneous polymerizable liquid mixture of monomer A, monomer B, and a pore-forming agent, is prepared using amounts sufficient to result in a homogeneous copolymer having the targeted EWC value.

In other aspects, the invention relates to homogeneous, copolymer xerogels or hydrogels, having predetermined EWC values, prepared by any of the methods disclosed herein; to articles shaped of such copolymers; to methods of preparing devices or structures utilizing such copolymers; and to the devices or structures per se.

Another aspect of the invention relates to a method for the preparation of a delivery device for the delayed/sustained release of an active agent therefrom e.g., a drug, which comprises:

a. introducing active agent and, optionally, a pharmaceutically acceptable carrier, into the core (reservoir) of the aforesaid cylindrically shaped copolymeric body in an amount sufficient for extended sustained release of said active agent into a delivery environment;

b. further introducing polymerizable liquid material into the said core in an amount sufficient to cover the active agent or to substantially or completely fill the core to the top of the cylindrical body, said polymerizable liquid material in its polymerized state having an equilibrium water content value which exceeds the equilibrium water content value of the cylindrical body; and c. polymerizing said polymerizable material to effectively seal the core opening with a plug (layer) of water-swellable, water-insoluble polymer.

In another aspect, the invention relates to a drug delivery device per se for the delayed/sustained release of an active agent to a delivery environment. The device comprises a hydrophilic copolymeric cartridge of xerogel or hydrogel described herein; hydrophilic sealing means to seal the open end of the cartridge thereby defining an enclosed core; an active agent (and optionally, a pharmaceutically acceptable carrier) contained in the core in an amount sufficient to be continually released over an extended period of time into a delivery environment; the said cartridge being characterized by water-swellability, water-insolubility, smooth, unscored outer and inner cylindrical surfaces, and a predetermined EWC value; and the said hydrophilic sealing means being characterized by water-swellability, water-insolubility, and an equilibrium water content value which exceeds that of said cartridge.

Another aspect of the invention relates to a kit for the implantation, desirably subcutaneously, of the aforesaid drug delivery device in an animal. The delivery device is amenable to long term implantation since degradation products are not dispersed throughout the body and the active compound is released in a relatively controlled manner into the delivery environment. The device being non-biodegradable remains intact and is retrievable; radioactive material can be used in the fabrication of the device or contained in the reservoir to facilitate location. In the form of a small rod defining a cylindrical core, preferably with a rounded or bullet-like shaped extremity, the drug delivery device can be packaged with a suitable hypodermic syringe-like instrument or a trocar as a sterilized kit tailored for the use(s) contemplated herein.

A further aspect of the invention relates to a method for introducing a cylindrically-shaped drug delivery device into an animal body by circular perforation to provide sustained release of a drug into said body which includes selecting an area of the body to be treated; implanting into the living tissues of the body the drug delivery device through a cannula of, for example, a trocar-like or hypodermic needle/syringe-like instrument; said delivery device comprised of a drug and, optionally, a pharmaceutically acceptable carrier sealed in a reservoir of a hydrophilic, rate-limiting cylindrically-shaped plastic article; and removing said cannula from said body.

OBJECTS OF THE INVENTIONS

Accordingly, one or more objects of the invention will be achieved by the practice of the inventions herein described.

It is an object of the invention to provide a method for centrifugally casting a cylindrical plastic article of good mechanical properties, said article being characterized by a cylindrical core, smooth unscored cylindrical surfaces, uniformity of thickness between said surfaces, and a predetermined EWC value.

It is another object of the invention to provide a drug delivery device for the delayed/sustained release of an active agent contained therein, said device characterized by improved surface characteristics and resistance to mineralization in vivo.

It is a further object of the invention to provide a drug delivery device comprised of an active compound (and optionally a pharmaceutically acceptable carrier) contained in the reservoir of a hollow cylindrical article which is characterized by a predetermined EWC value and sealed, at one end thereof, with unique leak proof closure means.

It is still another object of the invention to provide a disposable, sterilized kit comprising a drug delivery device hydrated to its predetermined EWC value, and injection means for the subcutaneous implantation of said device to a selected area of an animal body.

Another object of the invention is to provide reproducible hydrophilic cartridges, of predetermined EWC values and precise dimensions useful in the fabrication of drug delivery devices, by a simple, time-saving, and cost effective centrifugal casting method which comprises reacting unique polymerizable systems to form predetermined shaped homogeneous hydrophilic cartridges in situ, followed by postcuring and annealing steps, to yield relatively stress-free cartridges of good mechanical integrity.

It is another object of the invention to provide for the fabrication of xerogels or hydrogels useful as membranes, in particular, as cartridges characterized alia by a predetermined equilibrium water content value useful in drug delivery devices by a method which comprises polymerizing a monomeric mixture containing predetermined amounts of 2-hydroxyethyl methacrylate and a second hydrophilic monomer, e.g., hydroxypropyl methacrylate, to form a substantially homogeneous polymer (especially in terms of polarity), having the predetermined EWC value, void of deleterious nonpolar, hydrophobic regions, and of improved mechanical strength and elasticity.

A still further object of the invention is to provide a hydrophilic cartridge having a predetermined, targeted EWC value useful in drug delivery implants for the delayed/sustained release of a pharmaceutically acceptable amount of a drug to a body environment.

A yet further object of the invention is to provide thin, uniform, hydrophilic cartridges of predetermined EWC value and comprised of water-soluble, pore-forming agent(s) homogeneously distributed therein, said cartridges being useful in drug delivery implants, said agent(s) being removed by dissolving or leaching in an aqueous medium thus imparting a porous structure to said cartridge.

These and other objects will become apparent to those skilled in the art from a consideration of the specification.

BRIEF DESCRIPTION OF THE DRAWINGS

FIG. 1 is a side elevation view, partly in cross-section, of a polymerization column (tube) open at one end and closed with a Delrin ® plug at the other end and containing polymerizable material within its interior prior to mounting and rotating the column horizontally on a suitable machine.

FIG. 1a is a blown-up, side elevation view, in cross-section, of spindle plug assembly 20.

FIG. 2 is a partial side elevation view of a polymerization column horizontally mounted to a suitable lathe and containing a spin cast molded hydrophilic cartridge of predetermined dimensions within its core.

FIG. 3 is an enlarged side elevation, partly in cross-section, of a drug delivery device comprised of a drug and a pharmaceutically acceptable carrier contained in a cylindrically-shaped hydrophilic body.

In FIGS. 7-13, the release rates of a luteinizing hormone-releasing hormone, averaged over a seven day period, were normalized to an implant of 20 mm, standard reservoir length.

FIG. 7 is a graph showing in vitro release profile vs. time in days for LHRH-13 ($\mu$g/2 cm/day) through a cylindrically-shaped implant of crosslinked hydrophilic polyHPMA polymer at equilibrium water content. The scale on the ordinate axis (y-axis) was expanded four times to accommodate the extremely low release rate of LHRH-13. LHRH-13 is a luteinizing hormone releasing hormone polypeptide identified as [DHis(imBzl)$^6$ProNHEt]-[GnRH].

FIG. 8 is a graph showing in vitro release rate profile vs. time in days for LHRH-13 ($\mu$g/2 cm/day) through a cylindrically-shaped implant of crosslinked hydrophilic 35% HEMA/64.5 HPMA polymer at equilibrium water content.

FIG. 9 is a graph showing in vitro release rate profile vs. time in days for LHRH-13 ($\mu$g/2 cm/day) through a cylindrically-shaped implant of crosslinked hydrophilic 40% HEMA/59.5% HPMA polymer at equilibrium water content.

FIG. 10 is a graph showing in vitro release rate profile vs. time in days for LHRH-13 ($\mu$g/2 cm/day) through a cylindrically-shaped implant of crosslinked hydrophilic 50% HEMA/49.5% HPMA polymer at equilibrium water content.

FIG. 11 is a graph showing in vitro release rate profile vs. time in days for LHRH-13 ($\mu$g/2 cm/day) through a cylindrically-shaped implant of crosslinked hydrophilic 60% HENU/39.5% HPMA polymer at equilibrium water content.

FIG. 12 is a graph showing in vitro release rate profile vs. time in days for LHRH-13 ($\mu$g/2 cm/day) through a cylindrically-shaped implant of crosslinked hydrophilic 70% HENU/29.5% HPMA polymer at equilibrium water content.

FIG. 13 is a graph showing in vitro release rate profile vs. time in days for LHRH-40 ($\mu$g/2 cm/day) through a cylindrically-shaped implant of crosslinked hydrophilic polyHEMA polymer at equilibrium water content.

Figure 4:
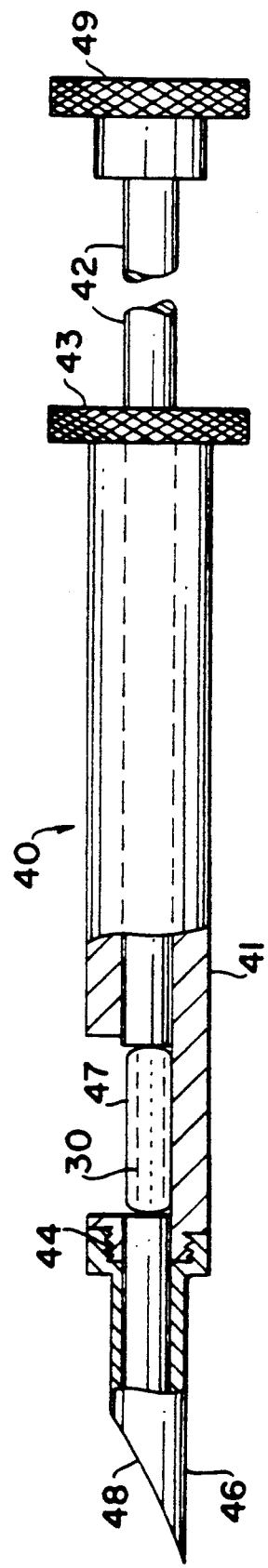
FIG. 4 is a side elevation view partly in cross section of a metal trocar containing a cylindrically-shaped drug delivery device for deposition to a preselected site of an animal.

Preferably the polymerization reaction is conducted in a polymerization column such as a suitable hollow tube fabricated of various materials such as plastics, e.g., polyethylene, polypropylene, and polystyrene; glass; and the like. Cross-sectional areas of the interior of the column are circular in shape and of equal diameter. In preferred embodiments, the column is fabricated from a material that will not significantly impede the transmission of radiation into the polymerization zone of the column. Glass, such as Pyrex ®, is a preferred material for the polymerization column when using radiation with/without initiation(s) and/or other catalyst(s).

Liquid polymerizable material useful in the manufacture of the novel hydrophilic products include a wide variety of polymerizable hydrophilic, ethylenically unsaturated compounds, in particular, hydrophilic monomers such as the monoester of an acrylic acid or methacrylic acid with a polyhydroxy compound having an esterifiable hydroxyl group and at least one additional hydroxyl group such as the monoalkylene and polyalkylene polyols of methacrylic acid and acrylic acid, e.g., 2-hydroxyethyl methacrylate and acrylate, diethylene glycol methacrylate and acrylate, propylene glycol methacrylate and acrylate, dipropylene glycol methacrylate and acrylate, glycidyl methacrylate and acrylate, glyceryl methacrylate and acrylate, and the like; the 2-alkenamides, e.g., acrylamide, methacrylamide, and the like; the N-alkyl and N,N-dialkyl substituted acrylamides and methacrylamides such as N-methylmethacrylamide, N,N-dimethylmethacrylamide, and the like; N-vinylpyrrolidone; the alkyl-substituted N-vinylpyrrolidones, e.g., methyl substituted N-vinylpyrrolidone; N-vinylcaprolactam; the alkyl-substituted N-vinylcaprolactam, e.g., N-vinyl-2-methylcaprolactam, N-vinyl-3,5-dimethylcaprolactam, and the like.

Mixtures of hydrophilic monomers are employed in the polymerization reaction. The type and proportion of monomers are selected to yield a homogeneous polymer, preferably a crosslinked homogeneous polymer, which on hydration possesses the desired EWC value for the contemplated application or use. This value can be predetermined by preparing a series of copolymers using different monomer ratios, e.g., mixtures of HENU and HPMA of varying ratios, ascertaining the EWC values of the copolymers, and plotting the relationship of % HPMA (or % HEMA) units in the HPMA/HEMA copolymers vs. weight percent EWC of the copolymers; see FIG. 6. The copolymers, shaped in the form of cylindrical implants and containing LHRH-13 in their core, can be hydrated and the relationship between in vitro elution rates ($\mu$g/2 cm/day) vs. the EWC value of each copolymer are then determined; see FIG. 6a.

In some instances the polymerization of certain hydrophilic monomeric mixtures may result in homogeneous hydrophilic copolymers which dissolve, to a varying extent, in an aqueous medium. In such cases, a small amount, e.g., up to 3 percent, of a copolymerizable polyethylenically unsaturated crosslinking agent can be included in the monomeric mixture to obtain homogeneous crosslinked copolymers which are water-insoluble as well as water-swellable. Slightly crosslinked homopolymer of HEMA has an EWC value of about 38%. Crosslinked copolymers of HENU and HPNU have EWC values below 38%. On the other hand, crosslinked copolymers of HEMA and acrylamide exhibit EWC values above 38 weight, e.g., upwards to approximately 75 weight %, and higher. Therefore, depending on the useful or effective elution rate of the active compound, e.g., drug, that is required of a hydrogel delivery system for a particular application, one skilled in the art, by following the teachings disclosed herein, can tailor-make copolymer hydrogel membranes which will elute the drug at the required rate. Preferred copolymers contain about 25 to 70 weight % of HEMA units and from about 75 to 30 weight % of units of a second ethylenic monomer and possess predetermined EWC values in the range of from about 25 to about 75 weight %. Highly preferred homogenous copolymers are those made from hydrophilic monomeric mixtures containing from about 30 to about 75 weight % HPMA, from about 70 to about 25 weight % HEMA, and a small amount of a polyethylenically unsaturated crosslinking agent, e.g., trimethylolpropane trimethacrylate ("TMPTMA").

Various aspects of the invention include homogeneous hydrophilic cartridges whose homogeneous polymer structure is formed via the polymerization of a mixture of hydrophilic monomers described previously; and the novel drug delivery device which utilize the homogeneous polymer cartridges in the delivery system. The polymerization of a mixture of hydrophilic monomers and hydrophobic monomers yields heterogeneous polymers. When hydrophobic segments are present in the polymer, the interfacial free energy increases thus enhancing protein adsorption and mineralization after implantation in an animal. Hydrogels of polyHEMA were measured to have interfacial free energy close to zero. According to the interfacial free energy interpretation, hydrogels of strictly hydrophilic components would strongly appear to be biocompatible with body tissue. Slightly crosslinked polyHEMA is a homogeneous, hydrophilic "homopolymer" (disregarding the relatively small quantities of polymerized crosslinking agent therein) of relatively fixed characteristics or values. Techniques of altering the "homopolymer" polyHEMA to impart to it additional characteristics or properties are difficult, time-consuming, and oftentimes result in erratic property behavior. On the other hand, mixtures of HEMA with varying quantities of other polymerizable hydrophilic comonomer(s) can be polymerized to give predictable homogeneous hydrophilic copolymers having (predetermined) tailor-made properties.

In one embodiment, a pore-forming material can be included with the polymerizable hydrophilic material. The pore-formers can be liquid or solid and are uniformly distributed or dispersed in the reaction medium. The pore-formers can be organic or inorganic and can be extracted from the resulting hydrophilic cartridge, by extraction or leaching, without any chemical change in the hydrophilic polymer. The pore-formers, in particulate form, can range in size from less than 0.1 micron to several microns depending on the porosity desired in the hydrophilic polymer. Illustrative pore-formers include sodium chloride, potassium phosphate, calcium nitrate, mono- and polysaccharides, and the like.

Useful crosslinking agents which can be included in the polymerizable reaction medium include, for example, the polyethylenically unsaturated compounds having at least two polymerizable ethylenic sites, such as the di-, tri- and tetra-ethylenically unsaturated compounds, in particular, the tri-unsaturated crosslinking agents with/without the di-unsaturated crosslinking compounds, for example, divinylbenzene, ethylene glycol dimethacrylate and diacrylate, propylene glycol dimethacrylate and diacrylate; and the di-, tri- and tetraacrylate or methacrylate esters of the following polyols: triethanolamine, glycerol, pentaerythritol, 1,1,1-trimethylolpropane; and others.

The polymerization reaction can be carried out in bulk or with an inert solvent. Suitable solvents include water; organic solvents such as water-soluble lower aliphatic monohydric alcohols as well as polyhydric alcohols, e.g., glycol, glycerine, dioxane, etc.; and mixtures thereof.

Compounds useful in the catalysis of the polymerizable ethylenically unsaturated compounds include the free-radical compounds and/or initiators of the type commonly used in vinyl polymerization such as the organic peroxides, percarbonates, hydrogen peroxides, and alkali metal sulfates. Illustrative examples include cumene hydroperoxide, t-butyl hydroperoxide, benzoyl peroxide, bis(4-t-butylcyclohexyl) peroxydicarbonate, hydrogen peroxide, 2,4-dichlorobenzoyl peroxide, acetyl peroxide, di-n-propyl peroxydicarbonate, di-t-butyl peroxide, di-sec-butyl peroxydicarbonate, ammonium sulfate, potassium sulfate, and sodium sulfate. A preferred catalyst is one which is effective at moderately low temperature such as at about 20°-80° C., such as tert-butyl peroctoate, benzoyl peroxide, and di(secbutyl) peroxydicarbonate.

A conventional redox polymerization catalyst can also be employed. The advantage of redox initiation is that the reaction occurs at reasonable rates at low temperatures, e.g., 0° C. to 50° C. A large number of reductant-oxidant pairs producing free radicals is known in the art. Examples include sodium bisulfate and ammonium persulfate, sodium thiosulfate and potassium persulfate, and the like.

Preferably, polymerization of the ethylenic compounds can be effected using radiation, e.g., U.V., X-Ray, gamma radiation, microwave, or other well-know forms of radiation. A preferred catalyst for U.V. cure is benzoin methyl ether.

Catalysts and/or initiators and/or radiation are employed in a catalytically effective amount to optimize the polymerization reaction.

In additional aspects, the hydrophilic cartridges, suitably stored in a dry environment, are utilized in the fabrication of the drug delivery device. A predetermined amount of an active compound per se or as an admixture with an inert, non-toxic material or as a suspension in a non-toxic medium, e.g., medical grade silicone oil, is introduced into the cartridge to partially fill the core. The top of the active compound is preferably covered with a layer of an inert material, e.g., teflon tape. The void in the core above the covering is thereafter sealed to prevent leakage into or out of the cartridge. Preferably this can be accomplished by introducing sufficient polymerizable material into the void to cover the layer of inert material or to substantially or completely fill the void and thereafter effecting a polymerization reaction to form a plug of water-swellable, water-insoluble polymer which seals the opening of the cartridge. The hydrophilic polymer plug, upon maximum hydration, will have an equilibrium water content value exceeding the equilibrium water content value of the hydrophilic cartridge. Using polymerizable material comprising ethylenically unsaturated monomer(s) and desirably crosslinking agent(s), a polymer plug grafted to the inner surface of the cartridge can be obtained.

By way of illustration, if the EWC value of the cartridge is less than about 38 weight % e.g., a cartridge consisting essentialy of HENU and HPMA units, the hydrophilic polymer plug can be crosslinked polyHEMA. If the EWC value of the cartridge is greater than 38 weight %, e.g., a cartridge consisting essentially of HEMA and acrylamide, the hydrophilic polymer plug can be crosslinked polyacrylamide.

In one embodiment, a hermetical closure of the cartridge can be accomplished in the following illustrative manner. The internal surface area of the core above the active compound or teflon tape, if used, is cleaned and slightly increased by careful reaming with an appropriate reamer. The reamed surface area is then cleaned with a sufficient amount of a mono- or polyhydric alcohol, e.g., $C_1$-$C_4$ alcohol such as ethanol, thereby causing a slight swelling of the surface. This technique promotes the penetration of the polymerizable hydrophilic material into the treated surface. Using a fine needle-syringe, a small amount of polymerizable material (desirably with initiator) is injected into the cartridge until the core is filled to the top. Preferably the polymerizable material will be of similar composition as that employed in the fabrication of the cartridge. The cartridge filled with active compound and polymerizable material, with its longitudinal axis perpendicular to the ground, is rotated on a suitable machine such as a lathe at a relatively low speed, e.g., 100 to 200 rpm, at ambient room temperature while exposed to radiation such as U.V. light for several minutes, e.g., 5-10 minutes. In the event the active compound, e.g., drug, is sensitive to U.V. light, a suitable shield such as aluminum foil can be used to shield the active compound from the U.V. light. The postcure step is effected at a temperature that is not detrimental to the drug. There is obtained a plug of hydrophilic polymer hermetically sealing the core opening. As will be apparent from the operative examples herein, the seal between the plug and the internal surface of the cartridge is stronger than the cartridge wall.

The inventions will become more apparent from the present disclosure when considered together with the accompanying drawings which are exemplary of aspects and embodiments thereof.

Referring to FIG. 1, there is disclosed a polymerization column 10 having a concentric cylindrical core 11 of smooth, unscored surface and which contains a predetermined amount of polymerizable hydrophilic liquid mixture 12 containing, for example, hydrophilic monomers, crosslinking agent, catalyst, and initiator. Removable Delrin ® plug 13 comprises head means 14 and stem means 16. Stem means 16, received in friction fit within core 11, seals one opening of column 10. Head means 14 is adapted to be received in hollow portion 17 and locked in collet chuck 18. A suitable machine such as a lathe with a motor of variable controlled speed (not shown) is connected to collet chuck 18 to provide for horizontal rotation of the column about its longitudinal axis A—A'. Spindle plug assembly 20 comprises outer plug 21, bearing shield 22, and inner plug 23 and is multifunctional. Inner plug 23 is snugly received within the inner race of ball bearing 24 which is also retained in proper relationship by securing means not shown. Outer plug 21 is adapted to be received in friction fit at opening 19 of the column. Bearing shield 22 functions as a protective shield for ball bearing 24. The outer race of ball bearing 24 is locked in chuck collet 26 of a lathe slide bar (not shown) adapted for left to right positioning and for insertion and withdrawal of outer plug 21 at opening 19.

The air space in the column defined by polymerization mixture 12 and opening 19 is gently purged with nitrogen using a syringe needle not shown. After purging, column 10 is sealed by inserting outer plug 21 into opening 19. The column, with its longitudinal axis parallel to the ground, is rotated at a speed, e.g., 2150 rpm, and ambient room temperature (approximately 22° C.), sufficient to cause radially outward displacement of the polymerizable liquid to its internal cylindrical surface thereby forming, upon stabilizing, a predetermined hollow cylinder of said liquid (a predetermined liquid cartridge shape). Ultra-violet light, not shown, is then directed at the shaped polymerizable liquid until it is polymerized to the predetermined cylindrically-shaped article with a concentric core.

Referring to FIG. 2, the internal surface of polymerization column 10 is contiguous to the external surface of a solid polymeric cartridge 31 which has an outer cylindrical surface and an inner smooth, unscored cylindrical surface 32 defining a substantially uniform wall thickness, i.e., $D_o - D_i = K$ wherein $D_o$ is the outer diameter of the cartridge, wherein $D_i$ is the inner diameter of the cartridge, and wherein K is a constant. The internal surface at base 33 is slightly oval in shape. Excess base 33 can be removed by cutting and its external surface polished to a oval-like cylindrical design.

FIG. 3 shows one form of a drug delivery device 30 of the invention. Cartridge 31 is shown with an oval-like base 33 (after trimming and polishing) packed with drug 34 in its core. The external and internal cylindrical surfaces of cartridge 30 are smooth and unscored. Teflon cover 36 separates drug 34 from hydrophilic plug 37, formed in situ from liquid material and polymerized to a solid hydrophilic plug 37. The equilibrium water content of plug 37 and thus its swellability are greater than the equilibrium water content of cartridge 31 therefore forming a hermetical seal upon hydration. The outer surface 38 of plug 37 including a portion of the contiguous cartridge wall 39 has been oval-shaped by trimming and polishing.

Referring to FIG. 4, one form for the implantation of a novel hydrated drug delivery device in an animal is shown. Trocar 40, a needle-syringe type instrument desirably fabricated of metal for injecting drug delivery device 30 into an animal comprises circular barrel 41 with a core for slidably receiving rod 42, retaining plate 43, and a threaded end 44 for accepting (disposable) threadable needle number 46. Drug delivery device 30 in a hydrated state rests in circular chamber 47. Needle member 46 having a hollow needle opening 48 is threaded at the end opposite opening 48 for acceptance to the main body of trocar 40. Sufficient steady forward pressure by hand on handle 49 causes rod 42 to eject drug delivery device 30 from chamber 47 through hollow needle opening 48 into a preselected body environment.

Figure 5:
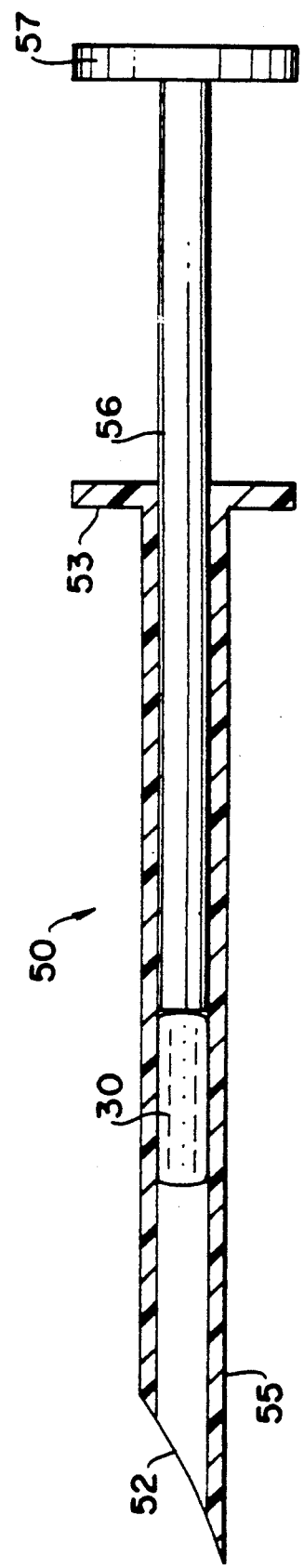
FIG. 5 is a side elevation view partly in cross section of a disposable plastic needle-like instrument with a drug delivery device within its barrel for the subcutaneous deposition by perforation to a preselected body part of an animal.

In FIG. 5 there is shown a simplified, disposable plastic trocar-type device 50 comprised of barrel 55 with hollow needle opening 52 at one end and retaining plate 53 at its other end, and rod 56 slidably received within the core of barrel 55. Trocar 40 and 50 can be fabricated of any material commonly used to inject a drug into an animal. After perforating the animal at the preselected site, sufficient steady forward hand pressure applied to handle 57 will cause rod 56 to eject drug delivery device 30 (contained in the core of the barrel) through needle opening 52 into the body environment. Alternatively, barrel 55 can be retracted from the body site by applying outward hand pressure on retaining plate 53 while maintaining rod 56 in its original fixed position with sufficient holding pressure. As barrel 55 is slowly retracted drug delivery device 30 will be deposited into the body site thorugh needle opening 52.

The novel drug delivery devices, in a preferred aspect, are highly useful in the delayed/sustained and the immediate/sustained release of active agents to animals, e.g., humans, sheep, dogs, cats, turkeys, cattle, etc. "Delayed/sustained release" is defined as delaying the release of an active agent until after placement in a delivery environment, followed by a sustained, preferably zero-order, release of the agent at a later time. "Immediate/sustained release" is defined as the commencement of the release of an active agent immediately or soon thereafter after placement in a delivery environment, followed by sustained release of the active agent. Other applications of the present invention include controlled delivery in industrial, agricultural and domestic settings.

In preferred aspects, the drug delivery devices of the invention are small cylindrically shaped implants containing within their core an active agent such as a macromolecular composition discussed herein, and optionally, a pharmaceutically acceptable carrier. The membrane thickness (between the interior and exterior and exterior surfaces) of the implant is substantially uniform, and serves as a rate-limiting barrier for the release of the contained agent. Such implants can be plasticized or hydrated and reshaped into other geometrically shaped articles for use in various medical applications. The hydrophilic implant as a xerogel, readily absorbs water. In a hydrated state it is referred to as a hydrogel. In either form, it is biocompatible and non-toxic to the host and non-biodegradable. It is, of course, water-swellable and water-insoluble. When the hydrogel attains its maximum level of hydration, the water content of the hydrogel is referred to as "equilibrium water content". The percent water content of the hydrogel (any state of hydration) is determined as follows:

$$\frac{\text{Weight of Hydrogel} - \text{Weight of Dry Polymer (Xerogel)}}{\text{Weight of Hydrogel}} \times 100$$

In the manufacture of the cylindrically-shaped device, several factors are considered. The release profile (delay time, release rate, and duration) is determined; the hydrophilic polymeric material is identified; and the diffusivity of the active agent through it (as a rate-limiting membrane) is measured. The hydration profile of the rate-limiting membrane for a given active agent may be readily determined by preparing a film of the selected polymer and subjecting it to a diffusion study, using a two compartment vertical glass cell, as is well known in the art.

The diffusion coefficient and the water content at which diffusion begins (i.e., below which substantially no diffusion occurs—hereinafter "$\%H_d$") are determined. A series of membranes is prepared from various polymers. The membranes are then hydrated to their capacity and their equilibrium water contents are measured. The fully hydrated membranes are placed in the two-compartment, vertical glass cells to measure and plot the diffusion of the macromolecular composition through the membrane materials at the various equilibrium water contents. The equilibrium water content of the most hydrated membrane through which no diffusion is detected (i.e., none of the active agent diffuses into the receptor cell) is the $\%H_d$ for the system being tested. This can be accomplished by plotting a curve of the permeability vs. equilbrium water content.

The permeability results (diffusion coefficients) are obtained according to Fick's First Law of Diffusion, by use of the equation:

$$\frac{dQ}{dt} = \frac{APC_d}{l}$$

wherein dQ/dt is the flux through the membrane material ($\mu g$/hr); it is measured as the slope of the linear part of the curve of cumulative transport versus time; wherein A is the area of the membrane (cm$^2$); wherein P is the membrane's permeability coefficient (cm$^2$/hr), or $DK_d$, wherein D is the diffusivity of the membrane (cm$^2$/hr), and $K_d$ is the partition coefficient for the membrane/donor solution; wherein l is the membrane thickness as measured at the end of the experiment (cm); and wherein $C_d$ is the concentration of the donor solution ($\mu g$/cm$^3$).

The release delay profile is then determined. Another series of polymeric membranes can be prepared, again varying the amounts of crosslinker and monomers. These membranes are then hydrated, but only partially, i.e., to a water content less than or equal to $\%H_d$. The partially hydrated membranes are placed in two-compartment vertical glass cells to measure and plot the diffusion of the active compound through the membranes versus time. Buffer solutions for the donor and receptor cells may be selected to contact the partially hydrated membranes and further hydrate them at approximately the same rate at which they will hydrate in the delivery environment. The time between commencement of the diffusion study, i.e., addition of the active agent to the donor cell, and the detection of a pharmaceutically effective concentration of the active agent in the receptor cell is the release delay time for that combination of polymer and initial percent hydration.

In order to determine the physical dimensions of the cylindrically-shaped device, the total amount of active agent to be delivered must be determined. This is the product of the desired daily dosage and the duration of delivery.

The volume of the cylindrical reservoir (core) of a cylindrically-shaped device is equal to $\pi r_i^2 h$ wherein $r_i$ is the radius of the reservoir and h is its height. The formula for steady state release from a cylinder is:

$$[dQ/dt] = [2\pi h DK_d C_d]/[\ln(r_o/r_i)]$$

wherein $r_o$ is the outside radius of the cylindrical device; and wherein $C_d$ is the concentration of drug in the donor solution, i.e., the carrier. Steady state release is obtained when $C_d$ is maintained at saturation. The thickness of the membrane needed for the desired sustained release is, therefore, $r_o - r_i$.

One aspect of the invention relates to a delivery device capable of delayed/sustained release of therapeutic dosages of an active agent into an aqueous delivery environment. The expression "active agent" ("active compound") as used herein broadly includes any compound or mixture thereof that can be delivered from the delivery device to produce a beneficial and useful result. The active agents whether in solid or liquid form will have sufficient solubility or miscibility in an aqueous system to render them capable of being released through the tailored-made hydrogel membranes into the delivery environment. The expressions "drug" including "macromolecular drug" as used herein include any physiologically or pharmacologically active substance that produces a localized or a systemic effect in animals. The active drugs that can be delivered include inorganic and organic drugs that act on the central nervous system, psychic energizers, tranquilizers, anticonvulsants, muscle relaxants, antiparkinson, analgesic, anti-inflammatory, anesthetic, antispasmodic, muscle contractants, anti-microbials, anti-malarials, hormonal agents, sympathomimetic, cardiovascular, diuretics, antiparasitic and the like.

The expression "macromolecular drug" as used herein is intended to include drugs, i.e., a substance that affects the activity of a specific bodily organ or function, having a molecular weight upwards to 25,000 and more, preferably greater than 1,000, preferably still from about 1,000 to about 25,000. Some drugs, e.g., steroids, anabolic agents and insulin, are characterized by a tendency toward aggregation with a resulting decrease in solubility. Suitable drugs include but are not limited to endocrine agents, chemotherapeutic agents, antibiotics, antidrug addiction agents, oncological treating agents, antifungal agents, antipulmonary disfunction agents, enzymes and macromolecular proteins affecting the central nervous system. Preferred macromolecular drugs include native and recombinant bioactive proteins and analogs thereof, such as (1) growth hormones and analogs thereof, (2) insulin and insulin-like growth factors such as somatomedins and analogs thereof and (3) other pituitary derived hormones such as prolactin and analogs thereof Hormonally active polypeptides are those peptides that have a specific regulatory effect on the activity of a certain body organ. Generally, they are secreted by an endocrine gland. Some peptides not secreted by an endocrine gland, however, exhibit a specific regulatory effect on a body organ and therefore are also classified as hormonally active compounds. Synthetically prepared analogs of naturally occurring hormonally active polypeptides and pharmaceutically acceptable salts of the naturally occurring hormones and their synthetic analogs that retain the same type of activity as their parent also are useful in the invention.

Hormonally active polypeptides comprise a diverse group of proteins but because of their functional specificity they can conveniently be grouped into discrete classifications by physiological effect. Each protein group generally regulates one specific physiological function by interacting only with the organ or organs directly affecting that function. For example, luteinizing hormone-releasing hormone (LH-RH)-active polypeptides act on the anterior pituitary gland to effect release of hormones that affect the activity of reproductive organs. Growth hormones act on the liver causing it to release somatomedin, the peptide factor responsible for skeletal growth. Thymosin and thymically active peptides interact with the autoimmune system, enhancing the ability of the body's immune system to combat disease. The naturally occurring luteinizing hormone-releasing hormone polypeptide and the synthetic analogs thereof are of particular interest for use in the novel delivery device.

The naturally occurring LH-RH peptide is produced in the hypothalmic region of the brain and controls the reproductive cycle of mammals by acting on the anterior pituitary gland to affect release of luteinizing hormone ("LH") and follicular stimulating hormone ("FSH"), which in turn act on the gonads to stimulate the synthesis of steroid hormones and to stimulate gamete maturation. The pulsatile release of LH-RH thereby controls the reproductive cycle in mammals. Additionally, LH-RH has effects in the placenta, in releasing human chorionic gonadotropin ("HCG"), and directly on the gonads.

Agonist analogs of LH-RH are useful for the control of fertility by two mechanisms of action. Low doses of LH-RH analogs can stimulate ovulation and are useful in the treatment of hypothalmic and ovulatory infertility. Additionally, they can be used for hypogonadal conditions and impotence, and for stimulating spermatogenesis and androgen production in the male.

Paradoxically, larger doses of highly potent and long-lasting analogs of LH-RH have an opposite effect, blocking ovulation in the female and suppressing spermatogenesis in the male. Related to these effects is a suppression of normal circulating levels of sexual steroids of gonadal origin, including reduction in accessory organ weight in the male and female. In domestic animals this paradoxical effect promotes weight gain in a feed-lot situation, stimulates abortion in pregnant animals and, in general, acts as a chemical sterilitant. A full list of the paradoxical high dose effects of LH-RH and its analogs is set out in U.S. Pat. No. 4,234,571.

There is also a group of LH-RH analogs termed antagonists. These polypeptides have the paradoxical effect shown by LH-RH agonists, but at low dose levels relative to naturally occurring LH-RH. Such compounds are included within the scope of the invention.

The natural LH-RH peptide is a hydrophilic decapeptide comprised of naturally occurring amino acids (which have the L-configuration except for the achiral amino acid glycine). Its sequence is as follows: (pyro)-Glu-His-Trp-Ser-Tyr-Gly-Leu-Arg-Pro-Gly-NH$_2$.

Another group of hormonally active polypeptides of interest herein are mammalian growth hormones. Growth hormones may be considered generally to be any substance which stimulates growth of the mammal when appropriately administered. The compounds of interest herein are those polypeptides secreted by the anterior pituitary gland, which exert an influence on protein, carbohydrate and lipid metabolism and control the rate of skeletal and visceral growth. Generally, growth hormones are species specific polypeptides with molecular weights falling between 22,000 and 24,000 daltons. In several species, for example, humans and cattle, the growth hormone also possesses some of the activities of lactogenic hormones.

Until recently, the availability of human growth hormone ("hGH") has been limited to that which could be extracted from the pituitary gland of human cadavers. However, recombinant DNA techniques have recently made it possible to produce biologically active hGH from bacteria in relatively substantial quantities.

Also contemplated are short-chain peptides of 10-13 amino acids that demonstrate thymic activity. A number of substances are known which, when administered to animals, enhance the ability of an organism's immune system to combat disease. Among these substances are crude extracts of myobacteria, glycopeptides and modifications of glycopeptides which are derived therefrom, and "thymosins," a family of hormones secreted by a thymosin gland.

The macromolecular compositions of this invention will be present in the delayed/sustained release compositions in varying amounts, depending upon the effect desired.

Treatment of infertility with synthetic LH-RH peptides requires a low level of drug, while reduction of fertility and related effects requires a large dose relative to the activity of naturally occurring LH-RH. For LH-RH agonist fertility control it is desired to release the drug at such a rate that the subject will receive between about 0.01 and 100 $\mu$g/kg body weight per day, preferably between 0.1 and 5.0 $\mu$g/kg body weight per day.

Human growth hormone quantities necessary to effect normal growth have not been precisely defined. HGH administered in amounts of about 0.1 to 10.0 Units (as defined by convention—based on biological activity for the particular hormone preparation—e.g., in one instance there are about 1.4 Units per mg of protein) per day based on body weight will effect increased linear growth in hGH-deficient children. A recent study by D. Rudman, et al. [*J. Clin. Endocrine Metabolism*, 49: 92-99 (1979)] has demonstrated the onset of increased linear growth in children known to be deficient in hGH and showing shorter stature and lower than average growth rates for their age groups by the administration of 0.3 to 3.0 Units of hGH per day.

Bovine, sheep or horse growth hormone may be administered on a daily basis in an amount anywhere between 5-100 mg/day. The dose may vary depending upon the activity of the growth hormone, the species, and the size of the animal.

Thymic peptides can be administered in the range of from about 10 ng/kg/day to about 20 mg/kg/day, preferably from about 100 ng/kg/day to about 5 mg/kg/day. Expressed in alternative terms for an average (70 kg) adult human subject, this would be from 700 ng/day to 1.4 g/day, preferably from 7 mg/day to 350 mg/day.

The amount of active agent employed will depend not only on the desired daily dose but also on the number of days that dose level is to be maintained. While this amount can be calculated empirically, the actual dose delivered is also a function of any interaction with materials and the carrier, if employed in the device.

In various embodiments, the novel drug delivery device may contain a pharmaceutically acceptable carrier which may be in the form of suspending media, solvents, aqueous systems, and solid substrates or matrices.

Suspending media and solvents useful as the carrier include, for example, oils such as silicone oil (particularly medical grade), corn oil, castor oil, peanut oil and sesame oil; condensation products of castor oil and ethylene oxide combining about 30 to 35 moles of ethylene oxide per mole of castor oil; liquid glyceryl triesters of a lower molecular weight fatty acid; lower alkanols; glycols; polyalkylene glycols.

The aqueous systems include, for example, sterile water, saline, dextrose, dextrose in water or saline, and the like. The presence of electrolytes in the aqueous systems may tend to lower the solubility of the macromolecular drug in them.

The solid substrates or matrices include, for example, starch, gelatin, sugars (e.g., glucose), natural gums (e.g., acacia, sodium alginate, carboxymethyl cellulose), and the like.

The carrier may also contain adjuvants such as preserving, stabilizing, wetting and emulsifying agents, and the like.

The hydrating liquid useful in the practice of the invention is typically a liquid simulating the environment in which the active compound will be released, e.g., body fluid, sterile water, tear fluid, physiological saline solution, phosphate buffer solution, and the like. While liquids other than water are useful as the hydrating liquid, the degree to which a hydrophilic membrane is hydrated is referred to as its "water content".

The devices of the invention(s) result in sustained release of the macromolecular drugs over extended periods of time. This time period may range from several days to a few years, for example, from one week to 3 years depending on the desired administration regimen. Preferably, the release time will be about 1 week to 18 months, and longer, it being understood that this time factor is a variable depending on the rate-releasing membrane of choice, its interconnecting pore structure, the active compound of choice, the solubility of the active compound in the liquid medium, and other considerations well known to those skilled in the art.

In operative Examples 2-20, hydrophilic cartridges were prepared by the rotational casting of polymerizable material in a tubular mold. The internal radius of the tube was approximately 1.2-1.3 mm. The tube was rotated about its longitudinal axis which was maintained parallel to the ground. Rotational speeds were of the order of 2150 rpm, though greater or lesser speeds could be used, e.g., 1000 rpm or less to 2500 rpm and more. The tubes were fabricated of polyethylene or polypropylene. When the polymerizable mixture within the spinning tube stabilized to the predetermined shape, U.V. light at a distance of less than one foot was then directed at the spinning tube for several minutes, e.g., about 7 minutes, to polymerize the mixture to the shaped product. The shaped product was cured and annealed as follows:

Thermal Cure: 60 minutes at 65° C.
Postcure: 30 minutes at 95° C.
Annealing: 30 minutes at 115° C. with gradual cooling to about 25° C.

After shaping and polishing the closed end of the cartridge to a oval-like cylindrical profile, there was obtained small cylindrically-shaped objects having smooth, unscored cylindrical surfaces. The dimensions of the cartridges were as follows: internal radius 0.8 mm; external radius 1.3 mm; length 25 mm.

In preferred embodiments, small drug delivery devices can be implanted subcutaneously in an animal by perforation. Such devices are characterized by a length of 10-30 mm, or less (e.g., 6-9 mm), an external diameter of 2-2.5 mm, or less (e.g., 1.5-1.9 mm), and an internal diameter of 1-1.2 mm, or less (e.g., 0.6-0.9 mm). The dimensions of the cartridge can vary outside of the limits stated above depending, in particular, on the medical application involved. Animals such as sheep, cows, goats, cattle, and large animals, in general, can tolerate implantation by perforation of larger dimensional drug delivery devices. Implantation can be effected by other means, e.g., open surgery.

Smooth, unscored cylindrically-shaped objects of varying lengths, e.g., up to 25 cm and longer, can also be prepared in accordance with the teachings herein. Such objects, in a hydrated state or plasticized with a non-toxic, biocompatible material, can be formed into desired shapes, e.g., a ring shape, for use as pessaries, surgical implants, etc. By the expressions "copolymer AB" or "copolymer AB consists essentially of monomer A units and monomer B units" is meant that the addition copolymerization of monomer A and monomer B has been effected through the polymerizable ethylenic bond of the said monomers. By way of illustration, if monomer A is 2-hydroxyethyl methacrylate and monomer B is N-methylacrylamide, copolymer AB contains recurring monomer A units, i.e.,

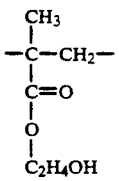

and recurring monomer B units, i.e.,

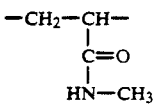

Whenever the term "%" or "percent" is used herein as in 50% HEMA/49.5% HPMA/0.5% TMPTMA, or % EWC, the meaning intended is "% by weight".

Unless the context indicates otherwise, the term "copolymer" includes polymers made by polymerizing a mixture of at least two ethylenically unsaturated monomers.

By the term "HEMA unit(s)" is meant the structure

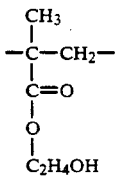

recurring in the polymer obtained by polymerizing hydrophilic material containing 2-hydroxyethyl methacrylate ("HEMA").

By the term "HPMA unit(s)" is meant the structure

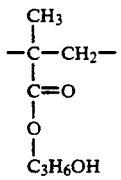

obtained by polymerizing hydrophilic material containing hydroxypropyl methacrylate ("HPMA").

EXAMPLE 1

A monomeric mixture comprising 90% 2-hydroxyethyl methacrylate, 5% methyl methacrylate, and 5% ethylene glycol dimethacrylate was prepared. All the monomers were previously purified by vacuum distillation. To the resulting mixture 0.2% benzoin methyl ether was added and stirred until dissolved. The mixture was deoxygenated by bubbling nitrogen through it for 10 minutes. To avoid premature polymerization the mixture was shielded from light. One end of a polypropylene tube (65 mm in length and $D_i$ of 2.5 mm) was plugged with a silicone sealant; the other end of the tube was sealed with a plug made by injecting a small amount of the above mixture, which was cured under a UV lamp for 5 minutes. Using a syringe filled with said mixture, the silicone plug was punctured and the tube was filled with the mixture to a height of about 10 mm from the top. The tube was inserted in a lathe collet and spun (spinning axis parallel to the ground) at about 2200 rpm. The centrifugal force created by the spinning tube caused the radially outward displacement of the mixture to assume a predetermined hollow cylindrical liquid configuration (i.e., a hollow tube of polymerizable liquid mixture). The spinning tube was then exposed to U.V. light for 7 minutes to polymerize the "liquid tube" to a solid hydrophilic tube (cartridge). The cartridge within the polypropylene tube was postcured for 14 hours at 65° C., followed with an additional 40 minutes at 105° C., and annealed at 116° C. for 40 minutes, and then slowly cooled to 22° C.

The cartridge was ejected from the tube, inspected for defects, and cut to a length of 30 mm. There was obtained a precisely dimensioned plastic cartridge fabricated of crosslinked heterogeneous 90% HEMA/5% MMA/5% EDGMA copolymer characterized by recurring hydrophilic and hydrophobic units. The weight of the cartridge was recorded. It was then filled with LHRH-13 (luteinizing hormone releasing hormone) by tightly packing it to a 20 mm height. The filled cartridge was weighed again to determine the weight of LHRH-13. The top of the drug was covered with a square of teflon tape. The remainder of the empty space of the cartridge was filled with the aforesaid monomeric mixture. Part of the cartridge containing LHRH-13 was covered with aluminum foil. The cartridge was then placed in the lathe and spun slowly (spinning axis of cartridge parallel to ground) under a UV lamp for 5 minutes to effect polymerization of the mixture. Postcuring of the polymer plug was effected by maintaining the cartridge at 50° C. for 18 hours. The end product was a drug delivery device.

The equibrium water content of the polymer cartridge was determined to be 28%. The drug delivery device was then subjected to an elution study in saline solution (10 ml per device) that was adjusted to pH 7 and preserved with 200 ppm of sodium azide. Samples were incubated in a shaker water bath at 37° C. The eluants were analyzed by HPLC on μBondapak C18 column at 7 day intervals. The elution rate of LHRH-13 from the device was determined to average approximately 13 μg/day over a one year period.

EXAMPLES 2-20

Following the general procedure described in the discussion of FIG. 1, several homogeneous hydrophilic cartridges were prepared using polyethylene tubes having a length of 48 mm and an internal diameter ($D_i$) of 2.6 mm. Each end of the tube were stoppered with a Delrin ® plug. Using a 250 μl syringe there was introduced 140 μl of polymerizable material into the open end of each tube. The remaining air space in the tube was gently purged with nitrogen using a syringe needle. Each tube, positioned, locked and sealed on the "Levin" lathe as described aforesaid was rotated with its longitudinal axis parallel to the ground at 2150 rpm until the polymerizable material stabilized to form a predetermined hollow cylindrical liquid configuration within the tube. U.V. light was then directed at the spinning tube for 7 minutes thereby causing the hollow cylindrical liquid configuration to polymerize to a solid configuration. The resulting shaped polymer was subjected to a thermal cure for 60 minutes at 65° C., a post cure for 30 minutes at 95° C., and an annealing treatment for 30 minutes at 115° C. followed by gradual cooling to ambient temperature (25° C.). Pertinent data including the equilibrium water content of the cartridges are set forth on Table I infra.

TABLE I

| Example | HEMA %[1] | HPMA %[2] | X-L %[3] | Catalyst[4] | E.W.C. %[5] |
|---|---|---|---|---|---|
| 2 | 99.5 | 0 | 0.5[6] | 0.4 | 37.5 |
| 3 | 89.0 | 10 | 1.0[7] | 0.4 | 35.2 |
| 4 | 79.0 | 20 | 1.0[7] | 0.4 | 33.6 |
| 5 | 70.0 | 29.5 | 0.5[6] | 0.4 | 33.1 |
| 6 | 60.0 | 39 | 1.0[7] | 0.4 | 30.5 |
| 7 | 50.0 | 49.5 | 0.5[6] | 0.4 | 30.1 |
| 8 | 45.0 | 54.5 | 0.5[6] | 0.4 | 29.5 |
| 9 | 40.0 | 59.5 | 0.5[6] | 0.4 | 28.7 |
| 10 | 40.0 | 59.2 | 0.8[6] | 0.4 | 28.2 |
| 11 | 35.0 | 64.5 | 0.5[6] | 0.4 | 27.7 |
| 12 | 30.0 | 69.5 | 0.5[6] | 0.4 | 27.6 |
| 13 | 30.0 | 69.0 | 1.0[6] | 0.4 | 27.3 |
| 14 | 30.0 | 68.5 | 1.5[6] | 0.4 | 25.7 |
| 15 | 30.0 | 68 | 2.0[6] | 0.4 | 25.1 |
| 16 | 25 | 74.5 | 0.5[6] | 0.4 | 26.3 |
| 17 | 20 | 79.5 | 0.5[6] | 0.4 | 26.0 |
| 18 | 10 | 89.5 | 1.0[6] | 0.4 | 24.5 |
| 19 | 10 | 89 | 1.0[7] | 0.4 | 24.1 |
| 20 | 0 | 99.5 | 0.5[6] | 0.4 | 22.9 |

[1]% by weight 2-hydroxyethyl methacrylate
[2]% by weight 3-hydroxypropyl methacrylate
[3]X-L represents % by weight of crosslinker
[4]0.3% by weight of benzoin methyl ether plus 0.1% by weight of bis(4-t-butylcyclohexyl) peroxydicarbonate
[5]Equilibrium water content
[6]Trimethylolpropane trimethacrylate
[7]Ethylene glycol dimethacrylate

EXAMPLES 21-31

A. Eleven cartridges were prepared from polymerizable monomeric mixtures comprising HEMA and/or HPMA and crosslinker. The equilibrium water content value (at ambient temperature, approximately 25° C.) was determined for each cartridge. The pertinent data are set forth below in Table II.

TABLE II

| Example | % HPMA Unit in Polymer[1] | E.W.C. %[2] | FIG.[3] |
|---|---|---|---|
| 21 | 0 | 37.5 | 13 |
| 22 | 29.5 | 32.8 | 12 |
| 23 | 49.5 | 30.2 | 10 |
| 24 | 54.5 | 29.5 | — |
| 25 | 59.5 | 28.4 | 9 |
| 26 | 64.5 | 27.7 | 8 |
| 27 | 69.5 | 26.9 | — |
| 28 | 74.5 | 26.3 | — |
| 29 | 79.5 | 25.8 | — |
| 30 | 89.5 | 24.5 | — |
| 31 | 99.5 | 22.9 | 7 |

[1]Weight % 3-hydroxypropyl methacrylate units in HEMA/HPMA polymer using 0.5 wt. % TMPTMA.
[2]% Equilibrium Water Content of the cartridge.
[3]Cartridge employed in the drug delivery device which was used to generate data on release rate profile versus time in days for LHRH noted in designated FIGS.

Figure 6:
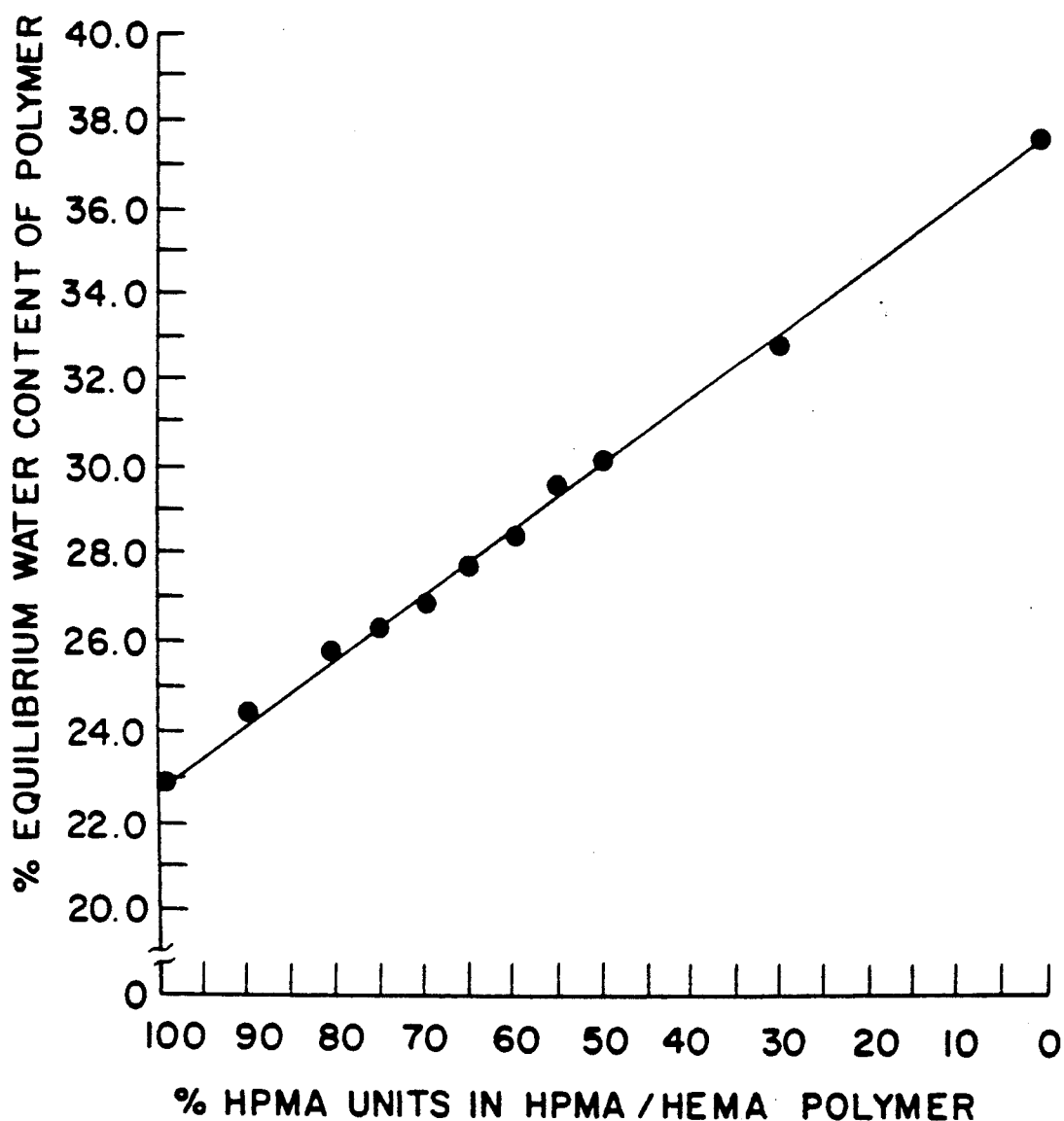
FIG. 6 is a graph showing the linear relationship between the equilibrium water content vs. the weight percent content of 3-hydroxypropyl methacrylate ("HPMA") units in crosslinked HENU/HPMA polymers at their maximum state of hydration.

With reference to FIG. 6, the linear relationship between the % equilibrium water content (EWC) (y axis) and HEMA units (Wt.%) in the HENU/HPNU copolymer (x axis) is graphically depicted. The slope m was determined from the relationship $\Delta y/\Delta x$ or $$\frac{y_2 - y_1}{x_2 - x_1},$$

using the coordinates (FIG. 6) for crosslinked polyHENU and crosslinked polyHPMA (or the coordinates for any two or more HEMA/HPMA copolymers having this linear relationship), the slope m was calculated from the above equation:

$$\frac{22.9 - 37.5}{0 - 100} = 0.146.$$

Referring to the general equation of a line, $y = mx + b$, the variable y represents the EWC (equilibrium water content) value, the variable x represents Wt. % HEMA units, and the constant b is replaced with the 22.9 (EWC value for polyHPMA). The result becomes:

$EWC = 0.146$ (Wt. % HEMA units) $+ 22.9$     Equation I

OR

Wt. % HEMA units $= \dfrac{EWC - 22.9}{0.146}$     Equation II

If the targeted EWC value of the crosslinked HEMA/HPMA copolymer is 30.2 weight %, a copolymer is prepared to yield a polymer composition of 50 HEMA units, 49.5 HPMA units, and 0.5 TMPTMA units. If a predetermined EWC value of 25.8% is desired, copolymerizable mixture of about 20% HEMA, 79.5% HPMA, and 0.5% TMPTMA would be employed to yield a hydrogel cartridge having this predetermined EWC value.

The crosslinked homogeneous HEMA/HPMA copolymers containing from about 30 to 75 weight % of HPMA units and from about 70 to 25 of HEMA units in the polymer chain and possessing predetermined EWC values in the range of from about 26 to about 33 weight % are particularly preferred as biocompatible, non-biodegradable, non-toxic hydrogel material for use in drug delivery devices, especially for the sustained release of LHRH and its analogs, as exemplified by LHRH-13, to the delivery environment. The homogeneous copolymers have extremely low interfacial free energy values and, in the practice of various aspects of the invention(s), body implants fabricated of such copolymers are biologically compatible with the body environment as evidenced by a lack of a thick, fibrous capsula on the implant. Homogeneous copolymers outside the above-stated preferred range are also useful, e.g., 90-10% HPMA/10-90% HEMA copolymers.

EXAMPLES 32-38

The release rates in vitro of LHRH-13 and LHRH-40 into an aqueous medium maintained at about 37° C. from several delivery devices (cylindrically shaped implants) sealed with a plug of polyHEMA were determined. The polyHEN" plug had an equilibrium water content value of 37.5% (at approximately 25° C.). The aqueous medium ("sink") was monitored every 7 days and the quantity of LHRH released from the implant was calculated to give average rates on a per day basis. All LHRH release data were normalized to a standard implant length of 10 mm. The cartridges used in the fabrications of the implants were prepared in the manner set forth in various preceding examples. The correlation of the cartridges and the implants is shown below:

TABLE III

| Implant[1] | Cartridge[1] | HPMA[2] | Polymer[3] | FIG. | EWC[6] | R.R.[7] |
|---|---|---|---|---|---|---|
| 32 | 20 | 99.5 | 0/99.5/0.5 | 7 | 22.9 | 0.8 |
| 33 | 11 | 64.5 | 35/64.5/0.5 | 8 | 27.7 | 16.8 |
| 34 | 9 | 59.5 | 40/59.5/0.5 | 9 | 28.4 | 20 |
| 35 | 7 | 49.5 | 50/49.5/0.5 | 10 | 30.2 | 37 |
| 36 | 6 | 39 | 60/39/1[4] | 11 | 30.5 | — |
| 37 | 5 | 29.5 | 70/29.5/0.5 | 12 | 32.8 | 50.5 |
| 38[5] | 2 | 0 | 99.5/0/0.5 | 13 | 37.5 | 1.5 |

[1] See Example.
[2] Weight % HPMA units in polymer.
[3] Make-up of polymer, % by wt. HEMA/HPMA/TMPTMA.
[4] EGDMA employed as the crosslinker in lieu of TMPTMA.
[5] Implant packed with LHRH-40; in Example 21-26 the implants were packed with LHRH-13.
[6] Weight % Equilibrium Water Content.
[7] Release rate or elution rate, μg/cm/day of LHRH (in vitro) into aqueous medium.

Figure 6A:
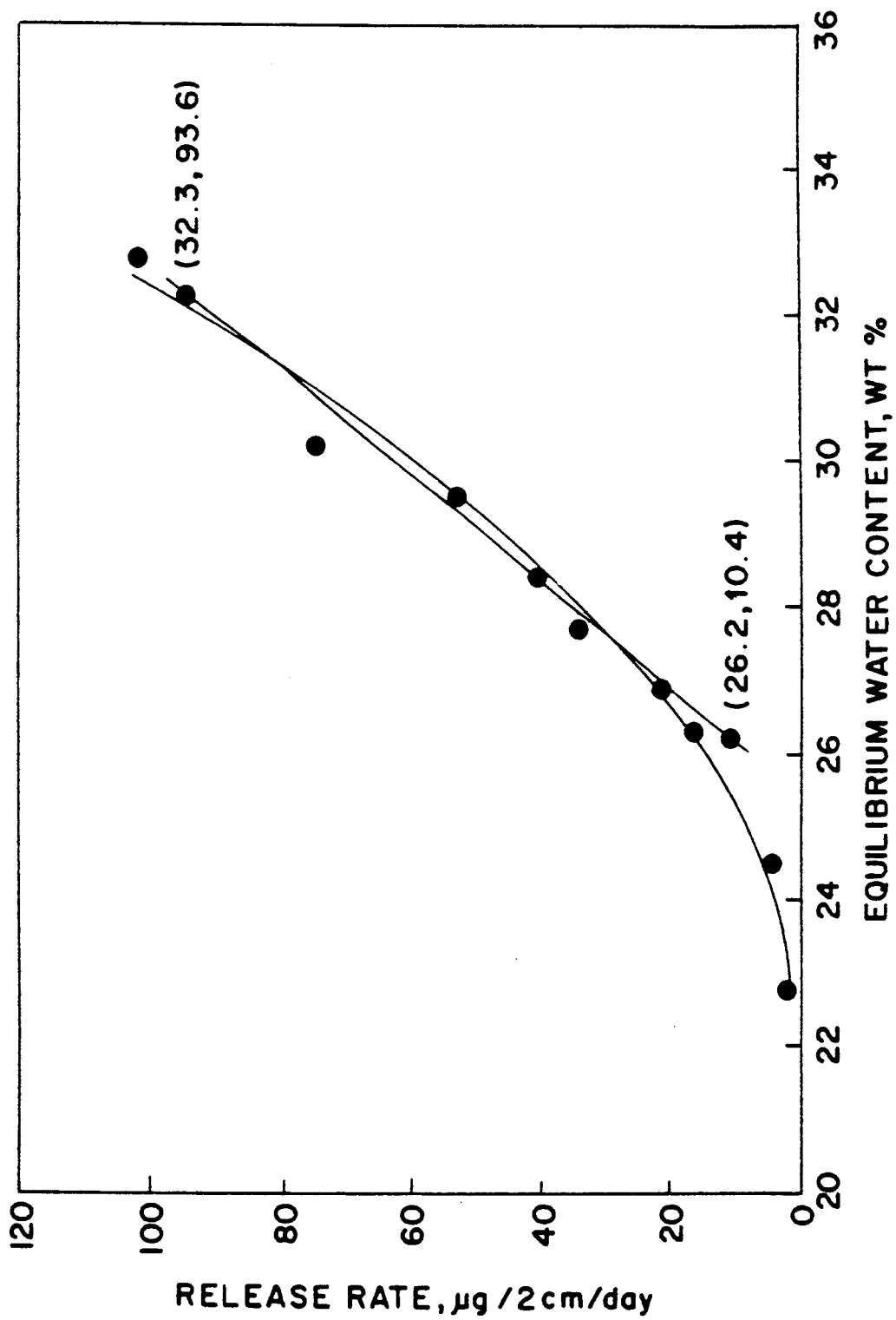
FIG. 6a is a graph showing in vitro release rate for LHRH ($\mu$g/2 cm/day) through cylindrically-shaped implants of various crosslinked hydrophilic HEMA/HPMA polymers vs. the equilibrium water content of the HEMA/HPNU polymers.
Figure 7:
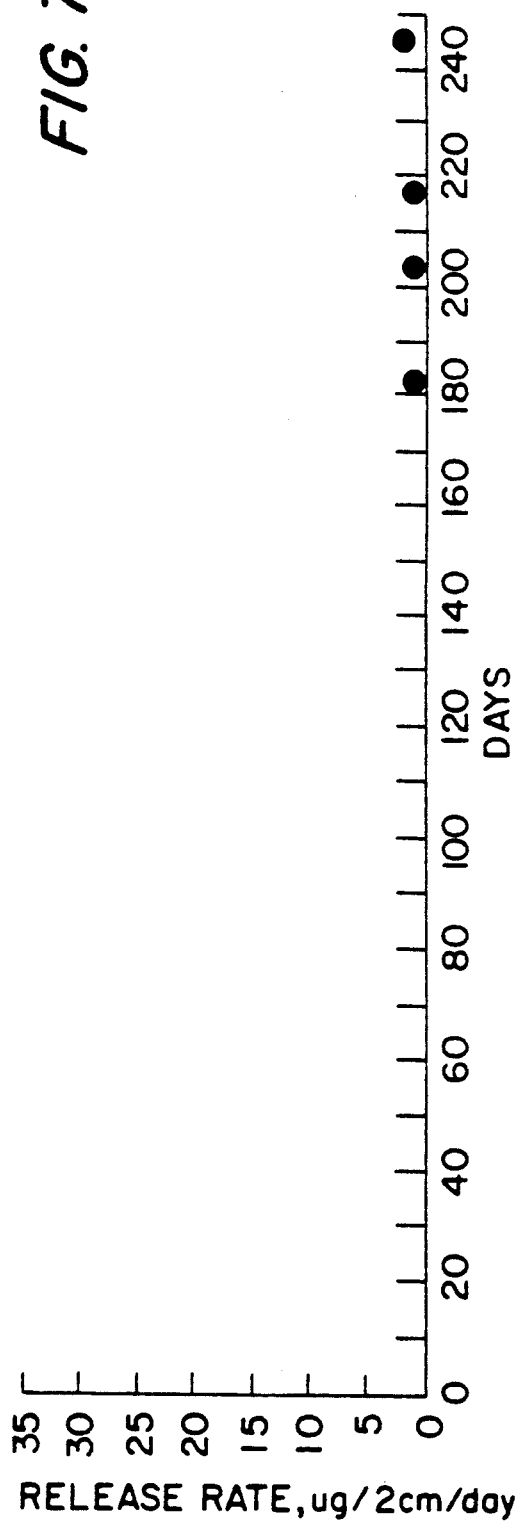
Figure 8:
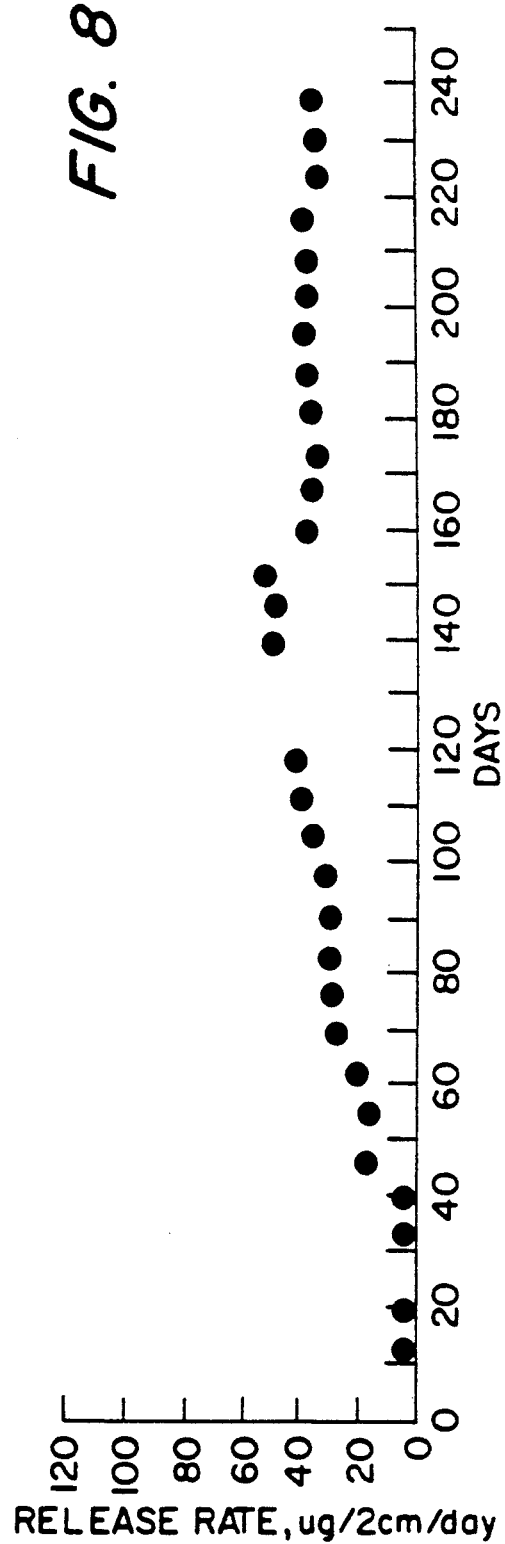

With reference to FIG. 6a, the relationship between the % EWC (x axis) of the hydrogel implant and release rate (RR) in vitro,4g/2 cm/day (y axis) is shown. The general linear portion of the curve was established and its slope -m was determined from the expression $$m = \frac{y - y_1}{x - x_1} = \frac{93.6 - 10.4}{32.3 - 26.2} = 13.64, \text{ or}$$

$m(x-x_1) = (y-y_1)$, wherein $y-y_1$ represent $\Delta y$ (release rate) and $x-x_1$ represents $\Delta x$ (EWC). Thus one arrives at the following equations:

$$13.64 (EWC - 26.2) = RR - 10.4 \quad \text{Equation III}$$

OR $$EWC = \frac{RR + 347}{13.64} \quad \text{Equation IV}$$

Substituting the value of EWC from Equation I for the EWC value of Equation IV, one arrives at Equation V:

$$0.146 \text{ (Wt. \% HEMA units)} + 22.9 = \frac{RR + 347}{13.64} \quad V$$

which on solving for Wt. % HEMA units one arrives at Equation VI:

$$\text{Wt. \% HEMA} = 0.5 (RR) + 17.40 \quad VI$$

Equation VI is most useful within a release rate of 10 to 100 μg/2 cm/day on the most linear portion of the curve shown in FIG. 6A.

By following the teachings herein disclosed, one having ordinary skill in this art can prepare homogeneous copolymers having a predetermined equilibrium water content (EWC). In turn, having established the composition of the copolymer (monomer A units and monomer B units) vis-a-vis the EWC, the artisan in turn can utilize the hydrogel in a diffusion device, e.g., a drug delivery device as described herein, through which a drug can diffuse at a predetermined rate.

EXAMPLE 39

Figure 14:
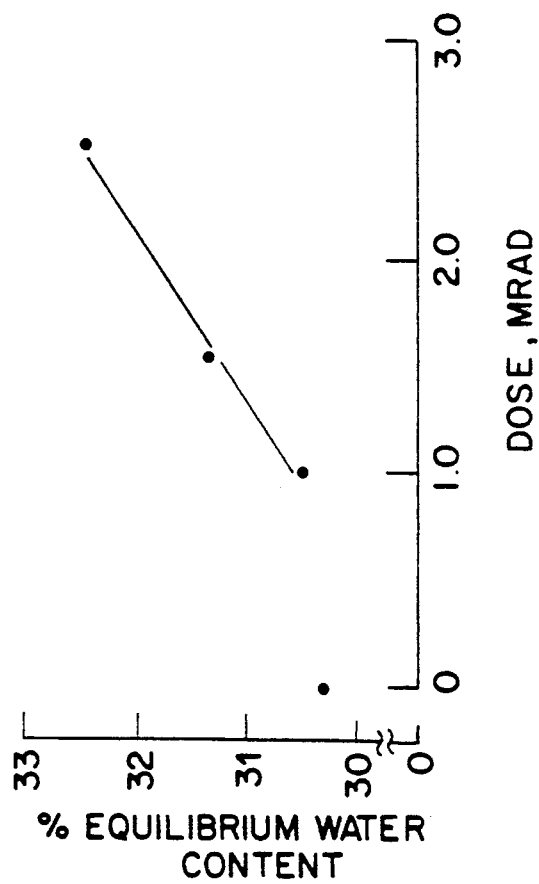
FIG. 14 is a graph showing the increase in equilibrium water content of a cylindrically-shaped implant of crosslinked hydrophilic 50% HEMA/49.5% HPMA polymer with increasing doses (in megarad) of irradiation over an eight hour period.
Figure 13:
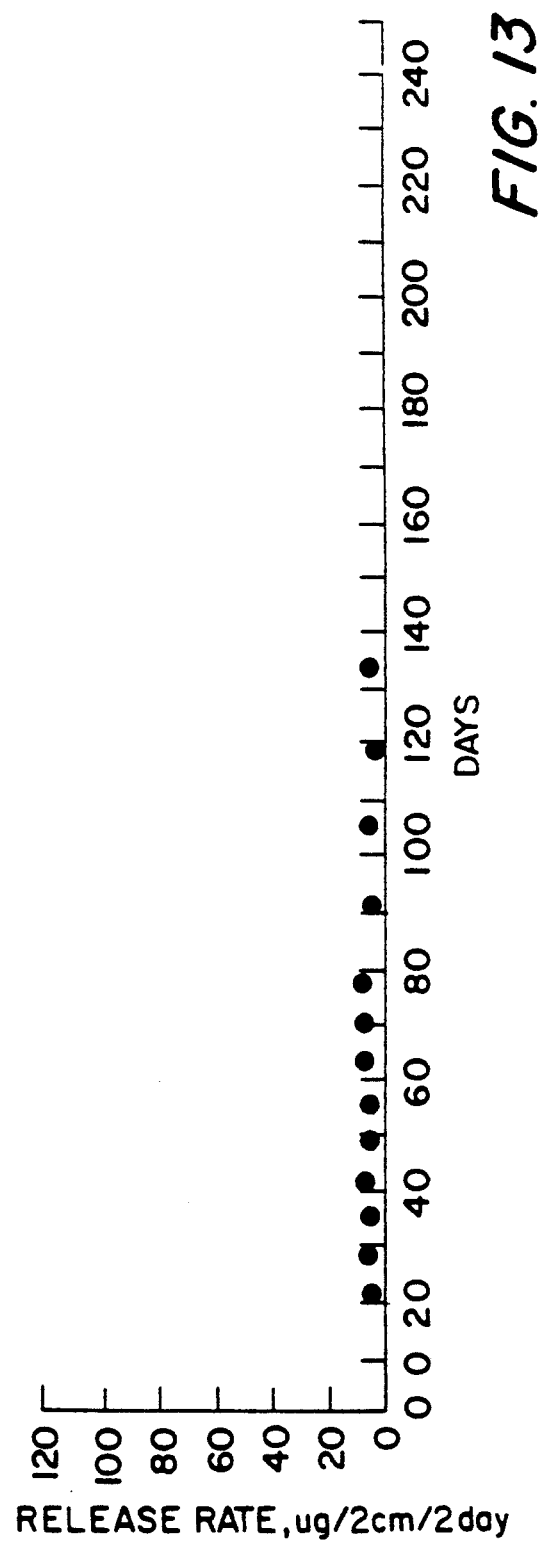
Figure 15:
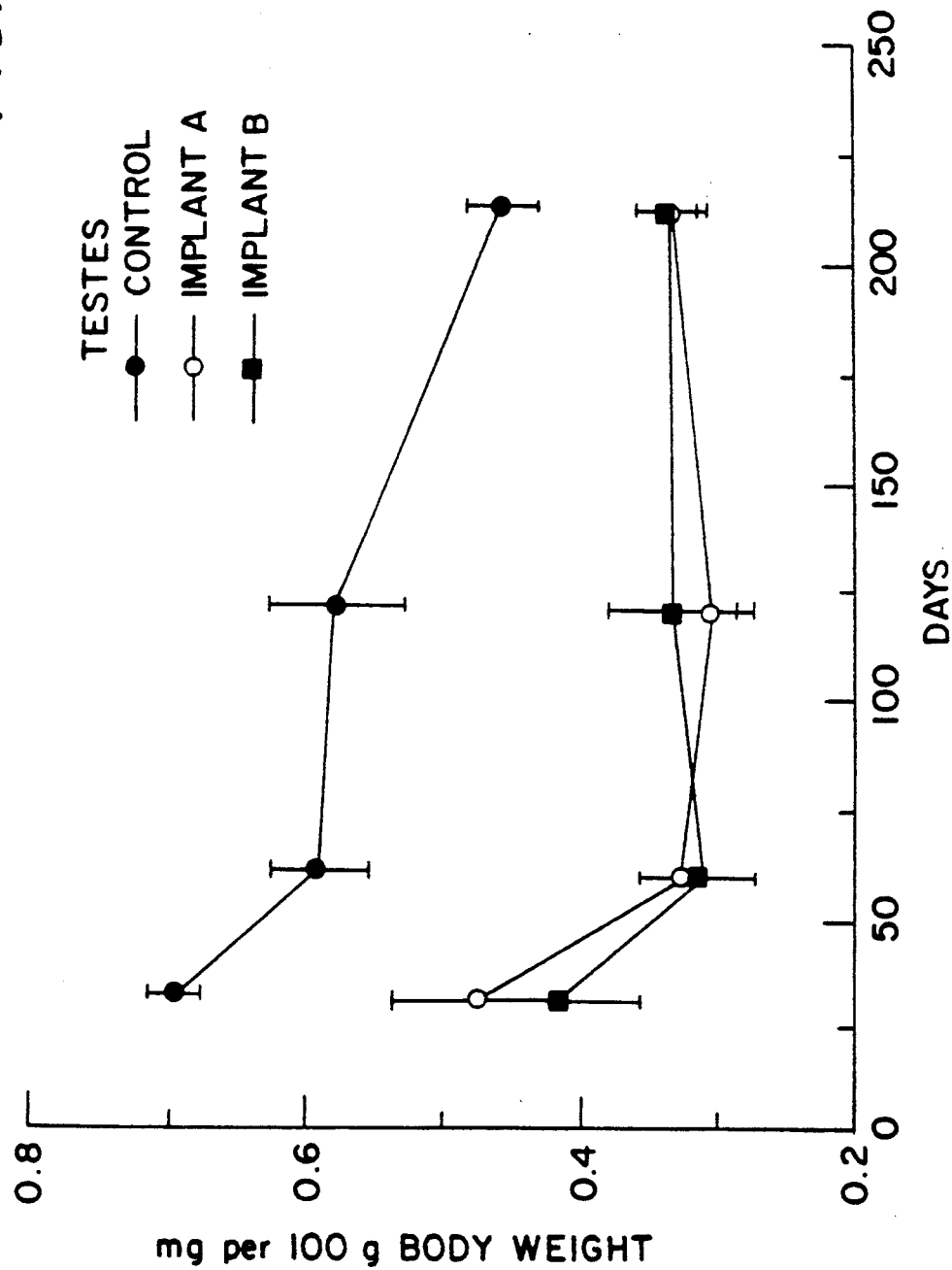
FIGS. 15 through 18 are graphs showing the in vivo release of LHRH-13 in rats from cylindrically-shaped delivery devices fabricated of crosslinked HENU/HPMA polymers and the effect on suppression of the testes and accessory sex glands. The hydrogel polymer of Implant A is 50% HEMA/49.5% HPMA/0.5% TMPTMA polymer and the hydrogel polymer of Implant B is 40% HEMA/59.5% HPMA/0.5% TMPTMA polymer.
Figure 16:
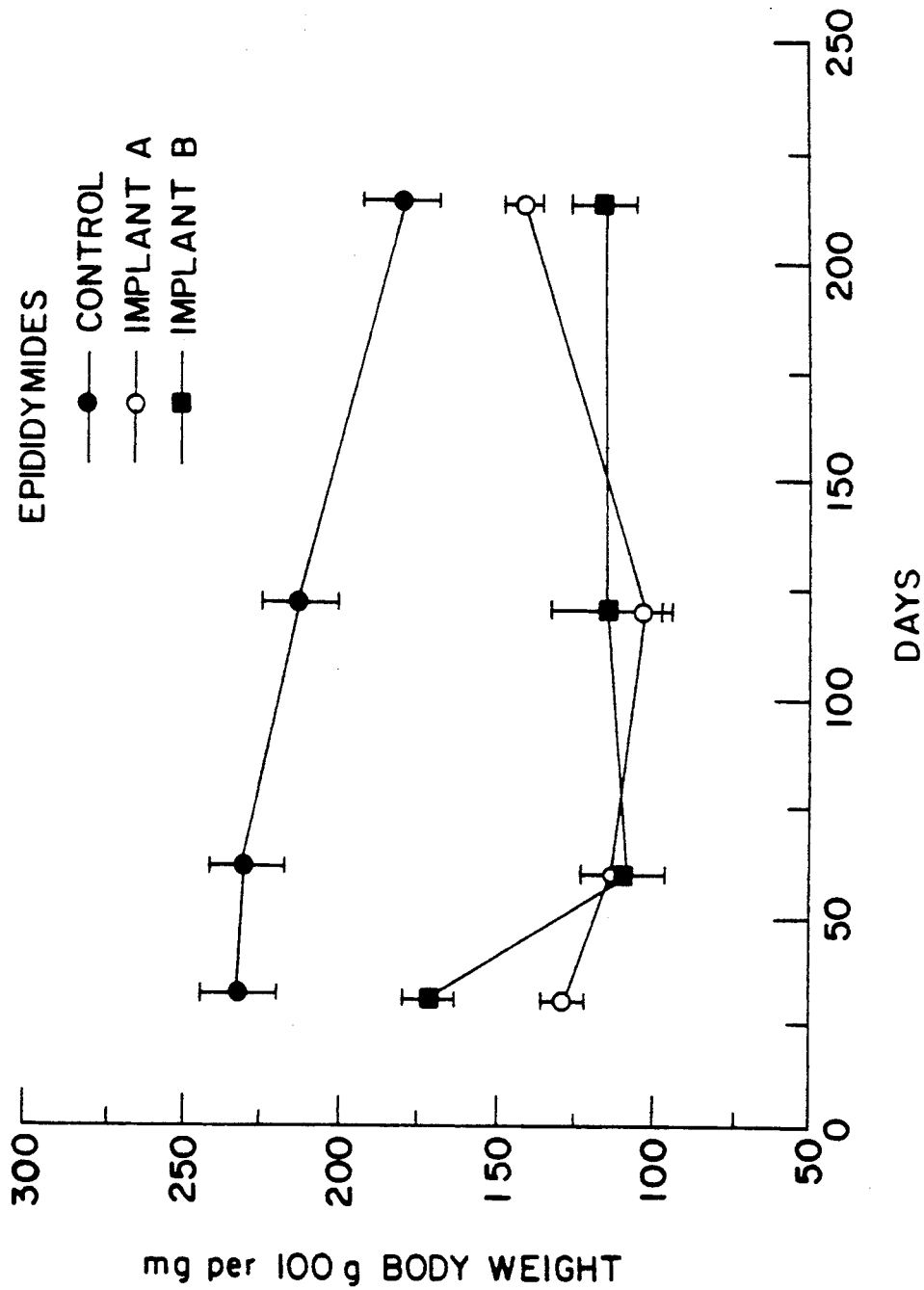
Figure 17:
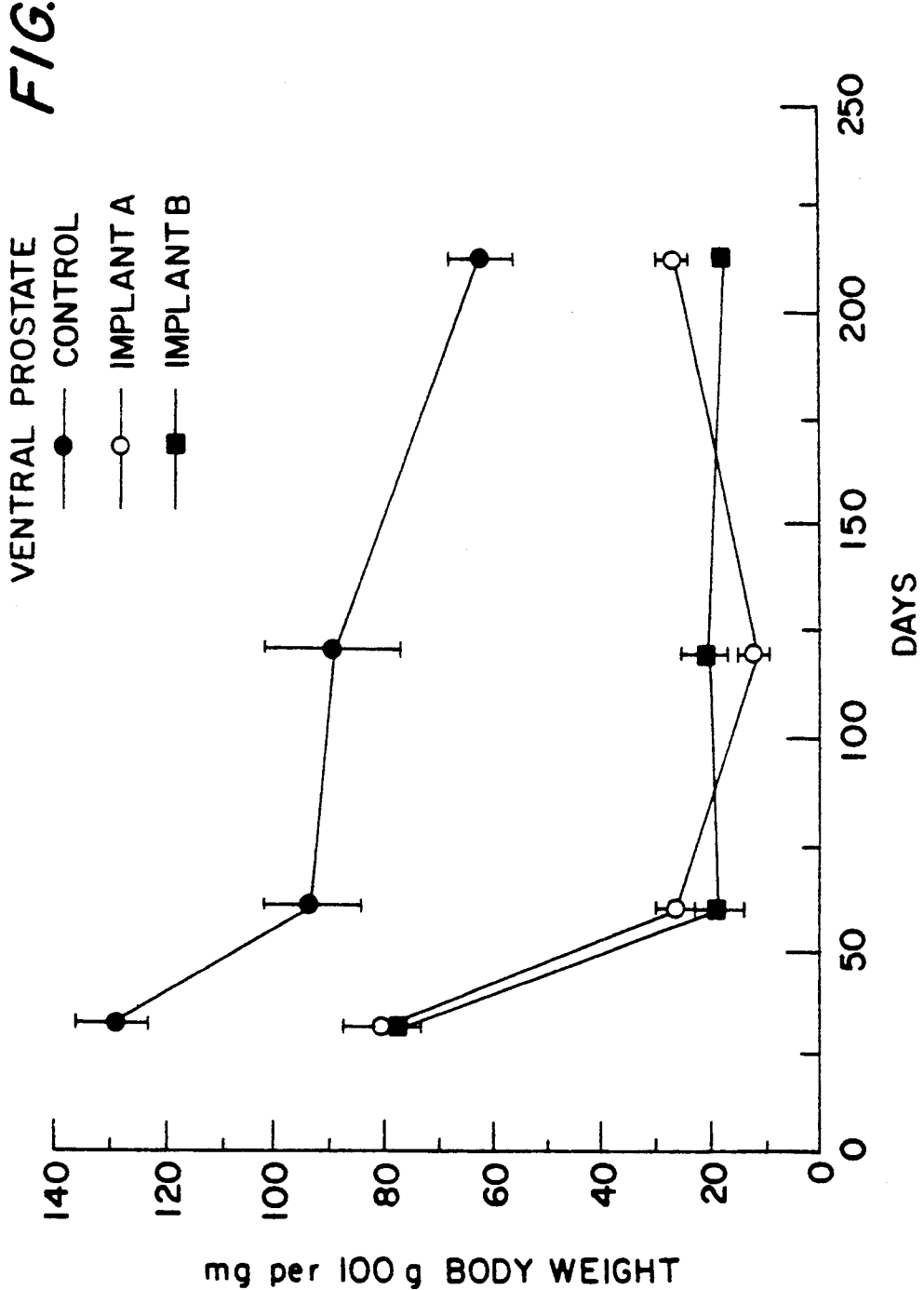
Figure 18:
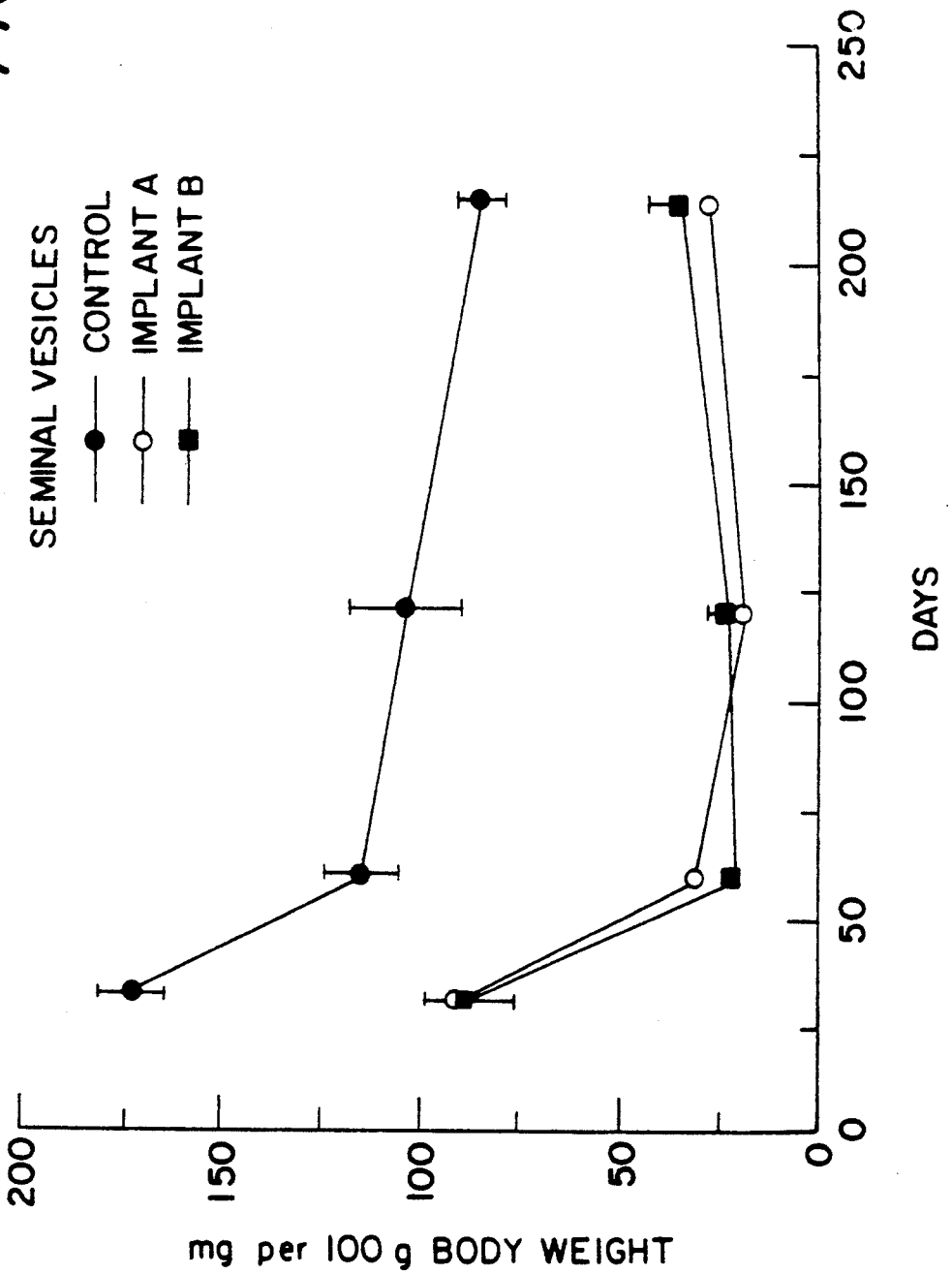

A 50% HEMA/49.5% HPMA/0.5% TMPTMA crosslinked polymer with an initial equilibrium water content of 30.2% was subjected to increasing doses of gamma-irradiation (in megarads) over an 8 hour period. FIG. 14 shows that % equilbrium water content of the polymer increased in a linearly relationship with increasing doses of irradiation. Test data confirmed that the release rate of LHRH-13 from hydrogel implants irradiated with 2.5 megarads was greater than that obtained from hydrogel implants irradiated with 1.0 megarads over similar periods.

EXAMPLES 40-43

Several cylindrically-shaped delivery devices designated as Implant A and Implant B, packed with LHRH-13 as described previously, were prepared for testing in rats to ascertain the effect on supression of the testes and accessory sex glands. Implant A is fabricated of 50% HEMA/49.5% HPMA/0.5% TMPTMA and Implant B of 40% HEMA/59.5% HPMA/0.5% TMPTMA. Implant A was implanted in one group of rats and Implant B was implanted in a second group of rats. Periodically, a designated number of rats were sacrificed and their testes, epididymides, ventral prostate, and seminal vesicles were weighed. The amount of LHRH-13 released from both Implants A and B were sufficient to suppress testicular and accessory sex glands and weights. In all instances, the weight suppressions exceeded that of the controls.

In FIGS. 15-18 there are shown graphically the weight of the testes, epididymides, ventral prostate, and seminal vesicles respectively, in mg per 100 g of rat weight vs. number of days. The rats were sacrificed at intervals of approximately 30, 60, 120 and 215 days.

Upon removal of the implants from the rats a few implants showed slight mineralization ascertained to be approximately calcium.

EXAMPLE 44

Cartridges fabricated from 4 different formulations were prepared. The data are set out in Table IV:

TABLE IV

| Formulation | HEMA % | HPMA % | TMPTMA % | BME %[1] | P-16 %[2] |
|---|---|---|---|---|---|
| 1 | 50 | 49.2 | 0.8 | 0.2 | 0.1 |
| 2 | 40 | 59.2 | 0.8 | 0.2 | 0.1 |
| 3 | 50 | 49.8 | 0.5 | 0.2 | 0.1 |
| 4 | 40 | 59.5 | 0.5 | 0.2 | 0.1 |

[1] Benzoin methyl ether.
[2] Bis(4-t-butylcyclohexyl)peroxydicarbonate.

A set of five cartridges (cylindrical wall thickness of 0.5 mm) were made from each of the 4 formulations noted above. The overall dimensions of the cartridges were equal. To each set of five cartridges there was added Poly B TM-411, a solid hydrophilic blue dye manufactured by Dynapol Co. and sold by Sigma Aldridge, Cat. No. 86172-3, and Sweet and Low ® Brand sugar substitute as an inert filler. The cartridges were sealed with a plug of crosslinked polyHEMA described previously. Each implant was then hydrated at room temperature in separate vessels containing 0.9 weight percent saline solution.

The blue dye, in solution, was unable to diffuse through the hydrogel membrane since its molecular size exceeded the permeability of the membrane.

The core of the 5 implants of each formulation swelled noticeably. By the third day the cylindrical wall of the five implants of Formulation 1 had burst. By the fourth day the cylindrical wall of the five implants of Formulation 2 implants had burst. By the fifth day the cylindrical wall of the five implants of Formulation 3 had burst. With respect to the Formulation 4 implants there remained 2 implants which were still intact on the seventh day, the cylindrical wall of the remaining 3 implants having burst on the sixth day. The bursting effect was evident by the dye seeping through the wall of the cylinder into the saline solution. In every instance, no leakage or bursting occurred at the interface of the polymer plug and the internal surface of the cartridge. The overall mechanical properties such as tensile strength, modulus, and elasticity were noticeably better with the implants of Formulation 3 and Formulation 4. This phenomenon could be attributable to the lesser concentration of tri-ethylenically unsaturated crosslinker employed.

What is claimed is:

1. A method for centrifugally casting a biocompatible copolymer having predetermined equilibrium water content (EWC) value formed by the addition polymerization of a mixture containing an ethylenically unsaturated hydrophilic monomer A and an ethylenically unsaturated hydrophilic monomer B copolymerizable therewith, said copolymer being useful as a hydrogen membrane in the diffusion therethrough of a selected active compound in an aqueous medium at a predetermined rate which comprises:
   a. determining the EWC values of hydrogel homopolymer of monomer A (homopolymer A) and hydrogel homopolymer of monomer B (homopolymer B);
   b. determining the relationship of the EWC values of the homogeneous hydrogel copolymers of mixtures of monomer A and monomer B (copolymers AB) versus the chemical composition of said copolymers AB;
   c. selecting the targeted EWC value and determining the chemical composition of homogeneous copolymer AB having this targeted EWC value;
   d. forming a polymerizable liquid mixture containing said monomer A and said monomer B in amounts sufficient to yield said homogeneous copolymer AB having the targeted EWC value;
   e. filling a tube comprising a core of smooth uniform cylindrical surface and closure means to prevent loss of the mixture during rotation, with a predetermined quantity of the liquid mixture;
   f. rotating the tube while maintaining a longitudinal axis of the tube parallel to the ground and effecting the rotation at a speed sufficient to cause radially outward displacement of the liquid monomers to assume a cylindrically-shaped liquid cartridge shape having a predetermined configuration within said tube;
   g. subjecting the tube to polymerization conditions to convert said liquid state cartridge to a predetermined solid state hollow plastic cartridge; and
   h. recovering a biocompatible, non-degradable, water-swellable, water-insoluble, homogeneous copolymer AB consisting essentially of monomer A units and monomer B units in the form of a cylindrical cartridge having walls of uniform thickness between its smooth external and internal cylindrical surfaces.

2. The method of claim 1 wherein said hydrophilic monomer A is 2-hydroxyethyl methacrylate, wherein said homogeneous copolymer AB consists essentially of from about 25 to 75 weight percent of 2-hydroxyethyl methacrylate units and from about 75 to 30 weight percent of monomer B units, and wherein the predetermined EWC value of the copolymer is in the range of about 25 weight % to about 75 weight %.

3. The method of claim 2 wherein said monomer B units are hydroxypropyl methacrylate units and wherein the predetermined EWC value of the copolymer is in the range of from about 26 to 33 weight %.

4. The method of claim 1 wherein said hydrophilic monomer A is 2-hydroxyethyl methacrylate, wherein said homogenous copolymer AB consists essentially of from about 25 to 70 weight percent of 2-hydroxyethyl methacrylate units and from about 75 to 30 weight percent of monomer B units, and wherein the predetermined EWC value of the copolymer is in the range of from about 25 weight % to about 75 weight %.

5. The method of claim 4 wherein said monomer B units are hydroxypropyl methacrylate units and wherein the predetermined EWC value of the copolymer is in the range of from about 26 to 33 weight %.

6. The method of claim 2 wherein said homogeneous copolymer AB is a xerogel.

7. The method of claim 2 wherein said homogeneous copolymer AB is a hydrogel.

8. The method for the preparation of a delivery device for the sustained release of an active agent therefrom which comprises:
   a. introducing active agent, and optionally a pharmaceutically acceptable carrier, into a cylindrically-shaped reservoir of a biocompatible, non-biodegradable, water-swellable, water-insoluble, cylindricialy-shaped plastic cartridge formed of copolymer AB according to claim 2, in an amount sufficient to provide extended sustained release of the active agent;
   b. introducing at least one polymerizable liquid monomer into the upper portion of said reservoir in an amount to completely fill the reservoir, said liquid monomer having an equilibrium water content value in its polymerized state which exceeds the equilibrium water content value of said plastic cartridge; and
   c. polymerizing said monomer to effectively seal the opening of the reservoir with a plug of water-swellable, water-insoluble polymer to form a delivery device which give a predetermined release of the active agent.

9. The method of claim 8 wherein said plastic cartridge has a smooth, oval cylindrical shape.

10. The method of claim 8 wherein the outer portion of the delivery device distal to the plug of polymer is subjected to a shaping step to impart a smooth oval shape thereto.

11. The method of claim 8 wherein said active agent is a drug.

12. The method of claim 11 wherein said drug includes native and recombinant bioactive proteins.

13. The method of claim 11 wherein said drug is a hormonally active polypeptide.

14. The method of claim 11 wherein said drug is luteinizing hormone-releasing hormone polypeptide.

15. The method of claim 1 wherein said drug is a mammalian growth hormone or mammalian growth releasing hormone.

16. The method of claim 8 wherein said plastic cartridge is a xerogel.

17. The method of claim 8 wherein said plastic cartridge is a hydrogel.

18. The method of claim 2 wherein said polymerizable liquid mixture contains a water-soluble pore-forming agent.

19. As an article, a biocompatible, non-biodegradable, water-swellable, water-insoluble, hydrophilic cartridge of copolymer AB defining a reservoir or core and useful as a rate-limiting barrier in a drug delivery device capable of being implanted in an animal by perforation, said cartridge characterized by a oval cylindrical shape at its closed end, and an open end distal to the closed end, smooth unscored internal and external cylindrical surfaces, a uniform thickness between said surfaces, said copolymer AB consisting essentially of from about 25 to 70 weight % of 2-hydroxyethyl methacrylate (monomer A) units and from about 75 to 30 weight % of monomer B units, and possessing a predetermined EWC value in the range of from about 25 to about 75 weight %.

20. The article of claim 19 wherein said monomer B units are hydroxypropyl methacrylate units.

21. The article of claim 20 wherein the plastic cartridge is in the state of a xerogel.

22. The article of claim 20 wherein the plastic cartridge is in a state of hydrogel.

23. The article of claim 19 wherein the plastic cartridge is a polymer of 2-hydroxyethyl methacrylate.

24. The article of claim 23 wherein the internal cylindrical surface area proximal to the open end of the cartridge has been scored and treated with a mono- or polyhydric alcohol to enhance graft polymerization of polymerizable ethylenically unsaturated monomer thereto.

25. A delivery device for the sustained release of an active agent therefrom which comprises:
   a. a biocompatible, non-biodegradable, water-swellable, water-insoluble, hydrophilic cartridge of copolymer AB defined in claim 19;
   b. sealant means for closure of the open end of the cartridge comprising a plug of biocompatible, non-biodegradable, water-swellable, water-insoluble, hydrophilic polymer having an equilibrium water content value greater than that of the cartridge per se; and
   c. an active agent contained in the reservoir of the cartridge in an amount sufficient to provide a predetermined sustained release thereof over an extended period of time.

26. The delivery device of claim 25 wherein said active agent is a drug.

27. The delivery device of claim 25 wherein said plastic cartridge and said sealant means are in the xerogel state.

28. The delivery device of claim 25 wherein said plastic cartridge and said sealant means are in the hydrogel state.

29. The delivery device of claim 25 wherein said active agent includes native and recombinant bioactive proteins.

30. The delivery device of claim 29 wherein said active agent is a hormonally active polypeptide.

31. The delivery device of claim 30 wherein said active agent is luteinizing hormone-releasing hormone polypeptide.

32. The delivery device of claim 25 wherein said active agent is a mammalian growth hormone or mammalian growth releasing hormone.

33. The delivery device of claim 31 wherein said delivery device contains a pharmaceutically acceptable carrier admixed with the active agent.

34. A method for the implantation of a small cylindrically-shaped delivery device into an animal for sustained release of an active agent therefrom which comprises:
   a. perforating the skin of an animal at a preselected site with an instrument comprising a hollow needle and the delivery device of claim 25;
   b. injecting said delivery device through said hollow needle and depositing it subcutaneously at the preselected site; and
   c. withdrawing said needle from the animal.

35. The method of claim 34 wherein said active agent comprises native or recombinant bioactive proteins.

36. The method of claim 35 wherein said active agent is a luteinizing hormone-releasing hormone polypeptide.

37. The method of claim 36 wherein the delivery device comprises a cartridge in a xerogel state.

38. The method of claim 36 wherein the delivery device comprises a cartridge in a hydrated state.

39. A kit useful for the implantation by perforation of a drug delivery device in an animal for sustained release of a drug therefrom comprising:
   a. the drug delivery device of claim 25;
   b. delivery means to eject said drug delivery device to the delivery environment of an animal; and
   c. container means to house said delivery device and said delivery means in a sterilized aqueous environment.

40. The kit of claim 39 wherein said delivery means comprises a small rigid hollow tube of uniform internal diameter having a needle-shaped opening at one end thereof, and a telescoping solid rigid rod slidably communicating with the internal surface of said tube, and wherein said drug delivery device positioned within said tube in proximity with one end of the rod for slidable ejection from said tube.

* * * * *

UNITED STATES PATENT AND TRADEMARK OFFICE
CERTIFICATE OF CORRECTION

PATENT NO. : 5,266,325
DATED : November 30, 1993
INVENTOR(S) : Petr Kuzma, Daniel G. Moro, Harry Quandt It is certified that error appears in the above-identified patent and that said Letters Patent is hereby corrected as shown below:

Col. 3, line 19, delete "occur ed" and substitute therefor -- occurred --.

Col. 5, line 36, delete "EGDNU" and substitute therefor -- EGDMA --.

Col. 5, line 39, delete "HENU" and substitute therefor -- HEMA --.

Col. 8, line 20, delete "alia" and substitute therefor -- inter alia --.

Col. 9, line 9, delete "HENU" and substitute therefor -- HEMA --.

Col. 9, line 15, delete "HPNU" and substitute therefor -- HPMA --.

Col. 9, line 47, delete "HENU" and substitute therefor -- HEMA --.

Col. 9, line 52, delete "HENU" and substitute therefor -- HEMA --.

Col. 9, line 66, delete "HENU/H-PMA" and substitute therefor -- HEMA/HPMA --.

Col. 10, line 47, delete "HENU" and substitute therefor -- HEMA --.

Col. 10, line 68, delete "HENU" and substitute therefor -- HEMA --.

Col. 10, line 68, delete "HPNU" and substitute therefor -- HPMA --.

Col. 12, line 29, delete "di(secbu-tyl)" and substitute therefor -- di(sec-butyl) --.

Col. 13, line 5, delete "HENU" and substitute therefor -- HEMA --.

UNITED STATES PATENT AND TRADEMARK OFFICE
CERTIFICATE OF CORRECTION

PATENT NO. : 5,266,325
DATED : November 30, 1993
INVENTOR(S) : Petr Kuzma, Daniel G. Moro, Harry Quandt It is certified that error appears in the above-identified patent and that said Letters Patent is hereby corrected as shown below:

Col. 23, line 68, delete "HENU/HPNU" and substitute therefor -- HEMA/HPMA --.

Col. 24, line 9, delete "HENU" and substitute therefor -- HEMA --.

Col. 24, line 62, delete "polyHEN"" and substitute therefor -- polyHEMA --.

Col. 25, line 23, delete "4g/2" and substitute therefor -- µg/2 --.

Col. 25, line 25, delete "-m" and substitute therefor -- m --.

Signed and Sealed this

Thirty-first Day of May, 1994

Attest:

BRUCE LEHMAN

Attesting Officer  Commissioner of Patents and Trademarks